US005591761A

United States Patent [19]

Chan et al.

[11] Patent Number: 5,591,761
[45] Date of Patent: *Jan. 7, 1997

[54] THIOPHENYL-, FURYL-AND PYRROLYL-SULFONAMIDES AND DERIVATIVES THEREOF THAT MODULATE THE ACTIVITY OF ENDOTHELIN

[75] Inventors: Ming F. Chan; Bore G. Raju; Adam Kois; Erik J. Verner; Chengde Wu; Rosario S. Castillo; Venkatachalapathi Yalamoori, all of San Diego; Vitukudi N. Balaji, Encinitas, all of Calif.

[73] Assignee: Texas Biotechnology Corporation, Houston, Tex.

[*] Notice: The portion of the term of this patent subsequent to May 20, 2014, has been disclaimed.

[21] Appl. No.: 222,287

[22] Filed: Apr. 5, 1994

Related U.S. Application Data

[63] Continuation-in-part of Ser. No. 142,552, Oct. 21, 1993, Pat. No. 5,514,691, Ser. No. 142,159, Oct. 21, 1993, Pat. No. 5,464,853, Ser. No. 142,631, Oct. 21, 1993, abandoned, Ser. No. 100,565, Jul. 30, 1993, abandoned, Ser. No. 100,125, Jul. 30, 1993, abandoned, and Ser. No. 65,202, May 20, 1993, abandoned, said Ser. No. 142,159, Ser. No. 142,552, and Ser. No. 142,631, each is a continuation-in-part of Ser. No.100,565, Ser. No. 100,125, and Ser. No. 65,202, said Ser. No. 100,565, and Ser. No. 100,125, each is a continuation-in-part of Ser. No.65,202.

[51] Int. Cl.$^6$ .......................... A61K 31/42; C07D 261/10
[52] U.S. Cl. ...................... 514/380; 514/311; 514/312; 514/313; 514/314; 514/378; 514/379; 546/153; 546/155; 546/159; 546/162; 546/167; 546/172; 548/241; 548/243; 548/244; 548/245; 548/247
[58] Field of Search .................... 548/241, 243, 548/244, 245, 247; 546/153, 155, 159, 162, 167, 172; 514/378, 379, 380, 311, 312, 313, 314

[56] References Cited

U.S. PATENT DOCUMENTS

| | | | |
|---|---|---|---|
| 3,300,488 | 1/1967 | Onoue et al. | 260/239.9 |
| 3,660,383 | 5/1972 | Sumimoto et al. | 260/239.9 |
| 4,752,613 | 6/1988 | Floyd et al. | 514/438 |
| 4,997,836 | 5/1991 | Sugihara et al. | 514/253 |
| 5,114,918 | 5/1992 | Isikawa et al. | 514/11 |
| 5,208,243 | 5/1993 | Peglion et al. | 514/309 |
| 5,270,313 | 12/1993 | Burri et al. | 514/253 |
| 5,292,740 | 3/1994 | Burri et al. | 514/256 |
| 5,378,715 | 1/1995 | Stein et al. | 514/329 |
| 5,389,620 | 2/1995 | Ishikawa et al. | 514/80 |
| 5,389,633 | 2/1995 | Miyake et al. | 514/233.2 |
| 5,407,941 | 4/1995 | Carceller et al. | 514/290 |
| 5,420,123 | 5/1995 | Murugesan | 514/220 |
| 5,420,129 | 5/1995 | Breu et al. | 514/252 |
| 5,420,131 | 5/1995 | Carceller et al. | 514/253 |
| 5,420,133 | 5/1995 | Dhanoa et al. | 514/256 |
| 5,420,138 | 5/1995 | Corbier et al. | 514/300 |
| 5,420,275 | 5/1995 | Masuya et al. | 544/236 |

FOREIGN PATENT DOCUMENTS

| | | |
|---|---|---|
| 5461286 | 3/1985 | Australia . |
| 2067288 | 10/1992 | Canada . |
| 2071193 | 12/1992 | Canada . |
| 0404525 | 12/1990 | European Pat. Off. . |
| 0405421 | 1/1991 | European Pat. Off. . |
| 0411150 | 2/1991 | European Pat. Off. . |
| 0436189 | 7/1991 | European Pat. Off. . |
| 0457195 | 11/1991 | European Pat. Off. . |
| 0460679 | 12/1991 | European Pat. Off. . |
| 0496452 | 7/1992 | European Pat. Off. . |
| 0558258 | 9/1993 | European Pat. Off. . |
| 0569193 | 11/1993 | European Pat. Off. . |
| 0640596 | 3/1995 | European Pat. Off. . |
| 60-188088 | 9/1985 | Japan . |
| 4134048 | 5/1992 | Japan . |
| 2259450 | 3/1993 | United Kingdom . |
| 9308799 | 5/1993 | WIPO . |

OTHER PUBLICATIONS

CA 120: 18233n The Discovery. . . –/–naphthalenesulfonamide Stein et al., pp. 21–22, 1994.

Ihara et al., "An endothelin receptor ($ET_A$) antagonist isolated from *Streptomyces Misakiensis*", *Biochem. and Biophys. Research Commun.*, 178(1):132–137 (1991).

Spinella et al., "Design and synthesis of a specific endothelin 1 antagonist: Effects on pulmonary vasoconstriction", *Proc. Natl. Acad. Sci. USA*, 88p:7443–7446 (1991).

Saeki et al.,"[$Ala^{1,3,11,15}$]endothelin-1 analogs with $ET_B$agonistic activity", *Biochem. and Biophys. Research Commun.*, 179(1):286–292 (1991).

Gu et al., "The inhibitory effect of [D–Arg$^1$, D–Phe, D–Try$^{7,}$ $_9$, Leu$^{11}$]substance P on endothelin–1 binding sites in rat cardiac membranes", *Biochem. and Biophys. Research Commun.*, 179(1):130–133 (1991).

Panek et al., "Endothelin and structurally related analogs distinguish between endothelin receptor subtypes", *Biochem. and Biophys. Research Commun.*, 183(2):566–571 (1992).

Ihara et al., "Biologicalprofiles of highly potent novel endothelin antagonists selective for the $ET_A$receptor", *Life Sciences*, 50:247–255 (1991).

(List continued on next page.)

*Primary Examiner*—Joseph K. McKane
*Attorney, Agent, or Firm*—Stephanie L. Seidman; Brown Martin Haller & McClain

[57] ABSTRACT

Thiophenyl-, furyl- and pyrrolyl-sulfonamides and methods for modulating or altering the activity of the endothelin family of peptides are provided. In particular, isoxazolyl-thiophenyl-sulfonamides, isoxazolyl-furyl-sulfonamides and isoxazolyl-pyrrolyl-sulfonamides and methods using these sulfonamides for inhibiting the binding of an endothelin peptide to an endothelin receptor by contacting the receptor with the sulfonamide are provided. Methods for treating endothelin-mediated disorders by administering effective amounts of one or more of these sulfonamides or prodrugs thereof that inhibit or increase the activity of endothelin are also provided.

93 Claims, No Drawings

OTHER PUBLICATIONS

Hirata et al., "Receptor binding activity and cytosolic free calcium response by synthetic endothelin analogs in culture rat vascular smooth muscle cells", *Biochem. and Biophys. Research Commun.*, 160:228–234 (1989).

Nakajima et al., "Synthesis of endothelin–1 analogues, endothelin–3, and sarafotoxin S6b: Structure–activity relationships", *J. of Cardiovascular Pharm.*, 13(Suppl. 5):S8–S12 (1989).

Yanagisawa et al., "A novel potent vasoconstrictor peptide produced by vascular endothelial cells", *Nature*, 332:411–415 (1988).

Kashiwabara et al., "Putative precursors of endothelin have less vasoconstrictor activity in vitro but a potent pressor effect in vivo", *FEBS Letters*, 247(1):73–76 (1989).

von Geldern et al., "A fluorogenic assay for endothelin–converting enzyme", *Peptide Research*, 4(1):32–35 (1991).

Inoue et al., "The human endothelin family: Three structurally and pharmacologically distinct isopeptides predicted by three separate genes", *Proc. Natl. Acad. Sci. USA*, 86:2863–2867 (1989).

Saida et al., "A novel peptide, vasoactive intestinal contractor, of a new (endothelin) peptide family", *J. Biol. Chem.*, 264(25):14613–14616 (1989).

Brooks et al., "Effect of nifedipine on cyclosporine A–induced nephrotoxicity, urinary endothelin excretion and renal endothelin receptor number", *Eur. J. of Pharmacology*, 194:115–117 (1991).

Bolger et al., "Vascular reactivity, tissue levels, and binding sites for endothelin: A comparison in the spontaneously hypertensive and Wistar–Kyoto rats", *Can. J. Physiol. Pharm.*, 69:406–413 (1990).

Simonson et al., "Endothelin–1 stimulates contraction of rat glomerular mesangial cells and potentiaties β–Adrenergic––mediated cyclic adenosine monophosphate accumulation", *J. Clin. Invest.*, 85:790–797 (1990).

Stewart et al., "Increased plasma endothelin–1 in pulmonary hypertension: Marker or mediator of disease?" *Annals of Internal Medicine*, 114(6):464–469 (1991).

Takayanagi et al., "Presence of non–selective type of endothelin receptor on vascular endothelium and its linkage to vasodilation", *FEBS Letters*, 282(1):103–106 (1991).

Nishikori et al., "Receptor binding affinity and biological activity of C–terminal elongated forms of endothelin–1", *Neurochem. Int.*, 18(4):535–539 (1991).

Castiglione et al., "Alanine scan of endothelin", Peptides: Chemistry and Biology, Proc. Amer. Rept. Symp. (Twelfth), J. A. Smith and J. E. Rivier, Eds. ESCOM, Leiden, 1992, pp. 402–403.

Galantino et al., "D–Amino acid scan of endothelin", Peptides: Chemistry & Biology, Proc. Amer. Report. Symp. (Twelfth), J. A. Smith and J. E. Rivier, Eds., ESCOM, Leiden, 1992, pp. 404–405.

Filep et al., "Endothelin–1 induces prostacyclin release from bovine aortic endothelial cells", *Biochem. and Biophys. Research Comm.*, 177(1):171–176 (1991).

Spokes et al., "Studies with endothelin–3 and endothelin–1 on rat blood pressure and isolated tissues: Evidence for multiple endothelin receptor subtypes", *J. of Cardiovascular Pharmacology*, 13(Suppl. 5):S191–S192 (1989).

Cardell et al., "Two functional endothelin receptors in guinea–pig pulmonary arteries", *Neurochem. Int.*, 18(4):571–574 (1991).

Borges et al., "Tissue selectivity of endothelin", *Eur. J. of Pharmacology*, 165:223–230 (1989).

Ogawa et al., "Molecular cloning of a non–isopeptide–selective human endothelin receptor", *Biochem. and Biophys. Research Comm.*, 178(1):248–255 (1991).

Schvartz et al., "Bovine cerebellum endothelin receptor: Solubilization and identification", *Endocrinology*, 126(6):3218–3222 (1990).

Saudek et al., "Solution conformation of endothelin–1 by $^1$H NMR, CD, and molecular modeling", *Int. J. Peptide Protein Res.*, 37:174–179 (1991).

Aumelas et al., "Determination of the structure of [Nle$^7$]–endothelin by $^1$H NMR", *Int. J. Peptide Protein Res.*, 37:315–324 (1991).

Perkins et al., "Proposed solution structure of endothelin", *Int. J. Peptide Protein Res.*, 36:128–133 (1990).

Spinella et al., "A proposed structural model of endothelin", *Peptide Research*, 2(4):286–291 (1989).

Saudek et al., "$^1$H–NMR study of endothelin, sequence–specific assignment of the spectrum and a solution structure", *FEBS Letters*, 257(1):145–148 (1989).

Ramachandran et al., "Conformation of polypeptides and proteins", *Adv. Prot. Chem.*, 23:283–437 (1968).

Szelke et al., "Novel transition–state analogue inhibitors of renin", In Peptides: Structure and Function, Proceeding of the Eighth American peptide symposium, (Hruby and Rich, Eds.); pp. 579–582, Pierce Chemical Co., Rockford, Illinois (1983).

Allen et al., "The Cambridge crystallographic data centre: Computer–based search, retrieval, analysis and display of Information", *Acta Crystallogr.*, B35:2331–2339 (1979).

Weiner et al., "A new force field for molecular mechanical simulation of nucleic acids and proteins", *J. Am. Chem. Soc.*, 106(3):765–784 (Eng.) (1984).

Cooper et al., "A novel approach to molecular similarity", *J. Comput.–Aided Mol. Design*, 3:253–259 (1989).

Brint et al., "Upperbound procedures for the identification of similar three–dimensional chemical structures", *J. Comput.–Aided Mol. Design*, 2:311–310 (1988).

Weiner et al., "An all atom force field for simulations of proteins and nucleic acids", *J. Comput. Chem.*, 7(2):230–252 (1986).

Karplus, M., "Molecular Dynamics: Applications to Proteins", in Computer Simulation of Chemical and Biomolecular Systems, (Bevendge and Jorfensen, Eds. ) *Annals of the New York Acad. Science*, 482:255–266 (1986).

Balasubramanian, R., "New type of representation for mapping chain folding in protein molecules", *Nature*, 266:856–857 (1977).

Kemp, D. S., "Peptidomimetrics and the template approach to nucleation of β–sheets and α–helices in peptides", *Tibtech*, 8:249–255 (1990).

Arai et al., "Cloning and expression of a cDNA encoding an endothelin receptor", *Nature*, 348:730–732 (1990).

De Nucci et al., "Pressor effects of circulating endothelin are limited by its removal in the pulmonary circulation and by the release of prostacyclin and endothelium–derived relaxing factor", *Proc. Natl. Acad. Sci.*, 85:9797 (1988).

Hiley et al., "Functional studies on endothelin catch up with molecular biology", *Trends Pharmacol. Sci.*10:47–49 (1989).

Kaltenbronn et al., "Renin inhibitors containing isosteric replacements of the amide bond connecting the P$_3$and P$_2$sites", *J. Med. Chem.*33:838–845 (1990).

Kloog et al., "Similarities in mode and sites of action of sarafotoxins and endothelins", *Trends Pharmacol. Sci.* 10:212–214 (1989).

Maggi et al., "Potent contractile effect of endothelin in isolated guinea–pig airways", *Eur. J. Pharmacol.* 160:179–182 (1989).

Martin et al., "Identification and characterization of endothelin binding sites in rat renal papillary and glomerular membranes", *Biochem. Biophys. Res. Commun.* 162:130–137 (1989).

Morel et al., "Increased plasma and pulmonary lymph levels of endothelin during endotoxin shock", *Eur. J. Pharm.* 167:427–428 (1989).

Palmer et al., "Nitric oxide release accounts for the biological activity of endothelium–derived relaxing factor", *Nature* 327:524–526 (1987).

Saito et al., "Application of monoclonal antibodies for endothelin to hypertensive research", *Hypertension* 15:734–738 (1990).

Sakurai et al., "Cloning of a cDNA encoding a non–isopeptide–selective subtype of the endothelin receptor", *Nature* 348:732–735 (1990).

Takayanagi et al., "Multiple subtypes of endothelin receptors in porcine tissues: characterization by ligand binding, affinity labeling and regional distribution", *Reg. Pep.* 32:23–37 (1991).

Tomita et al., "Plasma endothelin levels in patients with acute renal failure", *N. Engl. J. Med.* 321:1127 (1989).

Anagnostou et al., "Erythropoietin has mitogenic and positive chemotactic effects on endothelial cells", *P.N.A.S.* 87:5978–5982 (1990).

Buemi et al., "Influence of recombinant erythropoietin on the production of endothelin–1 from human umbilical artery", *Nephron* 64(1):165–166 (1993).

Carlini et al., "Intravenous erythropoietin (rHuEPO) administration increases plasma endothelin and blood pressure in hemodialysis patients", *Am. J. Hyper.* 6:103–107 (1993).

Clarke et al., "Endothelin is a potent long–lasting vasoconstrictor in men", *Am. J. Physiol.* 257(6 pt 2):H2033–H2035 (1989).

Eschbach et al., "Recombinant human erythropoietin in anemic patients with end stage renal disease; results of a phase III multicenter clinical trial", *Ann. Intern. Med.* 111:992–1000 (1989).

Heidenreich et al., "Erythropoietin induces contraction of isolated renal small resistance vessels", *Nephrol. Dial. Transplant* 5:739–740 (1990).

Hori et al., "Hemodynamics and volume changes by recombinant human erythropoietin (rHuEPO) in the treatment of anemic hemodialysis patients", *Clin. Nephrol.* 33:293–298 (1990).

Koyama et al., "Plasma endothelin levels in patients with uremia", *Lancet* 1(8645):991–992 (1989).

Nonnast–Daniel et al., "Atrial natriuretic peptide and central hemodynamics during correction of renal anemia by recombinant human erythropoietin treatment in regular dialysis treatment patients", *Nephrol Dial Transplant* 4:478 (1989).

Raine et al., "Effect of erythropoietin on blood pressure", *Am. J. Kid. Dis.* 18(suppl):76–83 (1991).

Samtleben et al., "Blood pressure change during treatment with recombinant human erythropoietin", *Contrib. Nephrol.* 66:114–122 (1988).

Schafer et al., "Treatment of renal anemia with recombinant human erythropoietin", *Am. J. Nephrol.* 8:352–362 (1989).

Sundal et al., "Correction of anemia of chronic renal failure with recombinant human erythropoietin:Safety and efficacy of one year's treatment in a European multicenter study of 150 hemodialysis–dependent patients", *Nephrol Dial Transplant* 4:979–987 (1989).

Tkayama et al., "Effects of recombinant human eryghropoietin on blood coagulation, fibrinolysis and endothelium in hemodialysis patients", *Blood Purif.* 1:53–54 (1991).

Yamashita et al., "Recombinant human erythropoietin (rHuEPO) induces high plasma endothelin (ET) levels in hemodialysis patients", *J. Am. Soc. Nephrol.* 1:409 (1990).

Ohashi et al., "Asterric acid, a new endothelin binding inhibitor", *J. Antibiotics* 45(10):1684–1685 (1992).

Williams et al., "Sarafotoxin S6c: An agonist which distinguishes between endothelin receptor subtypes", *Biochem. and Biophys. Research Commun.* 175(2):556–561 (1991).

Fujimoto, et al., "Isoxazole derivatives. II. Synthesis and structure of N-acylsufodiazoles and their homologs", *Chemical Abstracts*, vol. 65, No. 2, Jul. 18, 1966, Abstract No. 2241eq.

Stein, et al., "The Discovery of Sulfonamide Endothelin Antagonists and the Development of the Orally Active $ET_A$–Antagonist 5–(Dimethylamino)–N–(3-4–dimethyl–5–isoxazolyl)–1–naphthalenesulfonamide", *J. Med. Chem.* 37(3):329–331 (1994).

Doherty, "Endothelin: A new challenge", *J. Medicinal Chem.*, 35(9):1493–1508 (1992).

Bolger et al., "Characterization of binding of the Ca++ channel antagonist [$^3$H] nitrendipine, to guinea–pig ileal smooth muscle", *J. of Pharmacology and Experimental Therapeutics*, 225:291–309 (1983).

Shimazaki, et al., "Piperazine derivatives", *Chem. Abstracts* 106:558 (abst. No. 33114a) (1987).

Benigni, et al., "A specific endothelin subtype A receptor antagonist protects against injury in renal disease progression", *Kidney International* 44:440–444 (1993).

Cody, et al., "The rational design of a highly potent combined $ET_A$ and $ET_B$ receptor antagonist (PD145065) and related analogues", *Med. Chem. Res.* 3:154–162 (1993).

Fujimoto, et al., "A novel non–peptide endothelin antagonist isolated from bayberry", *FEBS* 305(1):41–44 (1992).

Ishikawa, et al., "Cyclic pentapeptide endothelin antagonists with high $ET_A$ selectivity. Potency–and solubility–enhancing modifications", *J. Med. Chem.* 35:2139–2142 (1992).

Miyata, et al., "WS009 A and B, new endothelin receptor antagonists isolated from *Streptomyces sp.* No. 89009", *J. Antibiotics* 45(7):1029–1040 (1992).

Miyata et al., "WS–7338, new endothelin receptor antagonists isolated from *Streptomyces sp.* No. 7338", *J. Antibiotics* 45(1):74–82 (1992).

Nakajima, et al., "Endothelin–binding inhibitors, BE–18257A and BE–18257B II. Structure determination", *J. Antibotics* 44(12):1348–1356 (1991).

Nishikibe et al., "Antihypertensive effect of a newly synthesized endothelin antagonist, BQ–123, in a genetic hypertensive model", *Life Sci.* 52:717–724 (1993).

THIOPHENYL-, FURYL-AND PYRROLYL-SULFONAMIDES AND DERIVATIVES THEREOF THAT MODULATE THE ACTIVITY OF ENDOTHELIN

RELATED APPLICATIONS

This application is a continuation-in-part of the following applications: U.S. application Ser. No. 08/142,552 to Chan et al., filed Oct. 21, 1993, entitled "N-(4-HALO-ISOXAZOLYL)-SULFONAMIDES AND DERIVATIVES THEREOF THAT MODULATE THE ACTIVITY OF ENDOTHELIN", now U.S. Pat. No. 5,514,691; U.S. application Ser. No. 08/142,159 to Chan et al., filed Oct. 21, 1993, entitled "N-(5-ISOXAZOLYL)BIPHENYLSULFONAMIDES, N-(3-ISOXAZOLYL)BIPHENYLSULFONAMIDES AND DERIVATIVES THEREOF THAT MODULATE THE ACTIVITY OF ENDOTHELIN", now U.S. Pat. No. 5,464,853; U.S. application Ser. No. 08/142,631 to Chan et al., filed Oct. 21, 1993, "N-(5-ISOXAZOLYL)-BENZENESULFONAMIDES, N-(3-ISOXAZOLYL)BENZENESULFONAMIDES AND DERIVATIVES THEREOF THAT MODULATE THE ACTIVITY OF ENDOTHELIN", now abandoned; U.S. application Ser. No. 08/100,565 to Chan et al., filed Jul. 30, 1993, entitled "N-(5-ISOXAZOLYL)SULFONAMIDES AND DERIVATIVES THEREOF THAT MODULATE THE ACTIVITY OF ENDOTHELIN", now abandoned; U.S. application Ser. No. 08/100,125 to Chan et al., filed Jul. 30, 1993, entitled "N-(3-ISOXAZOLYL)SULFONAMIDES AND DERIVATIVES THEREOF THAT MODULATE THE ACTIVITY OF ENDOTHELIN", now abandoned, and U.S. application Ser. No. 08/065,202, to Chan, filed May 20, 1993, entitled "SULFONAMIDES AND DERIVATIVES THEREOF THAT MODULATE THE ACTIVITY OF ENDOTHELIN", now abandoned.

U.S. application Ser. Nos. 08/142,159, 08/142,552, 08/142,631 are continuation-in-part applications of U.S. application Ser. Nos. 08/100,565, 08/100,125 and 08/065,202, and U.S. application Ser. Nos. 08/100,565 and 08/100,125 are continuation-in-part applications of U.S. application Ser. No. 08/065,202.

The subject matter of each of U.S. application Ser. Nos. 08/142, 159, 08/142,559, 08/142,631, 08/100,565, 08/100,125 and 08/065,202 is each incorporated herein in its entirety.

FIELD OF THE INVENTION

The present invention relates to the compounds that modulate the activity of the endothelin family of peptides. In particular, the invention relates to the use of sulfonamides and sulfonamide pro-drugs as endothelin agonists and antagonists.

BACKGROUND OF THE INVENTION

The vascular endothelium releases a variety of vasoactive substances, including the endothelium-derived vasoconstrictor peptide, endothelin (ET) (see, e.g., Vanhoutte et al. (1986) *Annual Rev. Physiol.* 48: 307–320; Furchgott and Zawadski (1980) *Nature* 288: 373–376). Endothelin, which was originally identified in the culture supernatant of porcine aortic endothelial cells (see, Yanagisawa et al. (1988) *Nature* 332:411–41 5), is a potent twenty-one amino acid peptide vasoconstrictor. It is the most potent vasopressor known and is produced by numerous cell types, including the cells of the endothelium, trachea, kidney and brain. Endothelin is synthesized as a two hundred and three amino acid precursor preproendothelin that contains a signal sequence which is cleaved by an endogenous protease to produce a thirty-eight (human) or thirty-nine (porcine) amino acid peptide. This intermediate, referred to as big endothelin, is processed in vivo to the mature biologically active form by a putative endothelin-converting enzyme (ECE) that appears to be a metal-dependent neutral protease (see, e.g., Kashiwabara et al. (1989) *FEBS Lttrs.* 247: 337–340). Cleavage is required for induction of physiological responses (see, e.g., von Geldern et al. (1991) *Peptide Res.* 4: 32–35). In porcine aortic endothelial cells, the thirty-nine amino acid intermediate, big endothelin, is hydrolyzed at the $Trp^{21}$-$Val^{22}$ bond to generate endothelin-1 and a C-terminal fragment. A similar cleavage occurs in human cells from a thirty-eight amino acid intermediate. Three distinct endothelin isopeptides, endothelin-1, endothelin-2 and endothelin-3, that exhibit potent vasoconstrictor activity have been identified.

The family of three isopeptides endothelin-1, endothelin-2 and endothelin-3 are encoded by a family of three genes (see, Inoue et al. (1989) *Proc. Natl. Acad. Sci. USA* 86: 2863–2867; see, also Saida et al. (1989) *J. Biol. Chem.* 264: 14613–14616). The nucleotide sequences of the three human genes are highly conserved within the region encoding the mature 21 amino acid peptides and the C-terminal portions of the peptides are identical. Endothelin-2 is ($Trp^6$, $Leu^7$) endothelin-1 and endothelin-3 is ($Thr^2$,$Phe^4$,$Thr^5$, $Tyr^6$,$Lys^7$,$Tyr^{14}$) endothelin-1. These peptides are, thus, highly conserved at the C-terminal ends.

Release of endothelins from cultured endothelial cells is modulated by a variety of chemical and physical stimuli and appears to be regulated at the level of transcription and/or translation. Expression of the gene encoding endothelin-1 is increased by chemical stimuli, including adrenaline, thrombin and $Ca^{2+}$ ionophore. The production and release of endothelin from the endothelium is stimulated by angiotensin II, vasopressin, endotoxin, cyclosporine and other factors (see, Brooks et al. (1991) *Eur. J. Pharm.* 194:115–117), and is inhibited by nitric oxide. Endothelial cells appear to secrete short-lived endothelium-derived relaxing factors (EDRF), including nitric oxide or a related substance (Palmer et al. (1987) *Nature* 327: 524–526), when stimulated by vaso-active agents, such as acetylcholine and bradykinin. Endothelin-induced vasoconstriction is also attenuated by atrial natriuretic peptide (ANP).

The endothelin peptides exhibit numerous biological activities in vitro and in vivo. Endothelin provokes a strong and sustained vasoconstriction in vivo in rats and in isolated vascular smooth muscle preparations; it also provokes the release of eicosanoids and endothelium-derived relaxing factor (EDRF) from perfused vascular beds. Intravenous administration of endothelin-1 and in vitro addition to vascular and other smooth muscle tissues produce long-lasting pressor effects and contraction, respectively (see, e.g., Bolger et al. (1991) *Can. J. Physiol. Pharmacol.* 69: 406–413). In isolated vascular strips, for example, endothelin-1 is a potent ($EC_{50}=4\times10^{-10}$M), slow acting, but persistent, contractile agent. In vivo, a single dose elevates blood pressure in about twenty to thirty minutes. Endothelin-induced vasoconstriction is not affected by antagonists to known neurotransmitters or hormonal factors, but is abolished by calcium channel antagonists. The effect of calcium channel antagonists, however, is most likely the result of inhibition of calcium influx, since calcium influx appears to be required for the long-lasting contractile response to endothelin.

Endothelin also mediates renin release, stimulates ANP release and induces a positive inotropic action in guinea pig atria. In the lung, endothelin-1 acts as a potent bronchoconstrictor (Maggi et al. (1989) *Eur. J. Pharmacol.* 160: 179–182). Endothelin increases renal vascular resistance, decreases renal blood flow, and decreases glomerular filtrate rate. It is a potent mitogen for glomerular mesangial cells and invokes the phosphoinoside cascade in such cells (Simonson et al. (1990) *J. Clin. Invest.* 85: 790–797).

There are specific high affinity binding sites (dissociation constants in the range of $2-6 \times 10^{-10}$M) for the endothelins in the vascular system and in other tissues, including the intestine, heart, lungs, kidneys, spleen, adrenal glands and brain. Binding is not inhibited by catecholamines, vasoactive peptides, neurotoxins or calcium channel antagonists. Endothelin binds and interacts with receptor sites that are distinct from other autonomic receptors and voltage dependent calcium channels. Competitive binding studies indicate that there are multiple classes of receptors with different affinities for the endothelin isopeptides. The sarafotoxins, a group of peptide toxins from the venom of the snake Atractaspis eingadensis that cause severe coronary vasospasm in snake bite victims, have structural and functional homology to endothelin-1 and bind competitively to the same cardiac membrane receptors (Kloog et al. (1989) *Trends Pharmacol. Sci.* 10: 212–214).

Two distinct endothelin receptors, designated $ET_A$ and $ET_B$, have been identified and DNA clones encoding each receptor have been isolated (Arai et al. (1990) *Nature* 348: 730–732; Sakurai et al. (1990) *Nature* 348: 732–735). Based on the amino acid sequences of the proteins encoded by the cloned DNA, it appears that each receptor contains seven membrane spanning domains and exhibits structural similarity to G-protein-coupled membrane proteins. Messenger RNA encoding both receptors has been detected in a variety of tissues, including heart, lung, kidney and brain. The distribution of receptor subtypes is tissue specific (Martin et al. (1989) *Biochem. Biophys. Res. Commun.* 162: 130–137). $ET_A$ receptors appear to be selective for endothelin-1 and are predominant in cardiovascular tissues. $ET_B$ receptors are predominant in noncardiovascular tissues, including the central nervous system and kidney, and interact with the three endothelin isopeptides (Sakurai et al. (1990) *Nature* 348: 732–734). In addition, $ET_A$ receptors occur on vascular smooth muscle, are linked to vasoconstriction and have been associated with cardiovascular, renal and central nervous system diseases; whereas $ET_B$ receptors are located on the vascular endothelium, linked to vasodilation (Takayanagi et al. (1991) *FEBS Lttrs.* 282: 103–106) and have been associated with bronchoconstrictive disorders.

By virtue of the distribution of receptor types and the differential affinity of each isopeptide for each receptor type, the activity of the endothelin isopeptides varies in different tissues. For example, endothelin-1 inhibits $^{125}$I-labelled endothelin-1 binding in cardiovascular tissues forty to seven hundred times more potently than endothelin-3. $^{125}$I-labelled endothelin-1 binding in non-cardiovascular tissues, such as kidney, adrenal gland, and cerebellum, is inhibited to the same extent by endothelin-1 and endothelin-3, which indicates that $ET_A$ receptors predominate in cardiovascular tissues and $ET_B$ receptors predominate in non-cardiovascular tissues.

Endothelin plasma levels are elevated in certain disease states. Endothelin-1 plasma levels in healthy individuals, as measured by radioimmunoassay (RIA), are about 0.26–5 pg/ml. Blood levels of endothelin-1 and its precursor, big endothelin, are elevated in shock, myocardial infarction, vasospastic angina, kidney failure and a variety of connective tissue disorders. In patients undergoing hemodialysis or kidney transplantation or suffering from cardiogenic shock, myocardial infarction or pulmonary hypertension levels are as high as 35 pg/ml have been observed (see, Stewart et al. (1991) *Annals Internal Med.* 114: 464–469). Because endothelin is likely to be a local, rather than a systemic, regulating factor, it is probable that the levels of endothelin at the endothelium/smooth muscle interface are much higher than circulating levels.

Endothelin agonists and antagonists

Because endothelin is associated with certain disease states and is implicated in numerous physiological effects, compounds that can interfere with or potentiate endothelin-associated activities, such as endothelin-receptor interaction and vasoconstrictor activity, are of interest. A limited number of compounds that exhibit endothelin antagonistic activity have been identified. In particular, a fermentation product of *Streptomyces misakiensis*, designated BE-18257B, has been identified as an $ET_A$ receptor antagonist. BE-18257B is a cyclic pentapeptide, cyclo(D-Glu-L-Ala-allo-D-lle-L-Leu-D-Trp), which inhibits $^{125}$I-labelled endothelin-1 binding in cardiovascular tissues in a concentration-dependent manner ($IC_{50}$ 1.4 µM in aortic smooth muscle, 0.8 µM in ventricle membranes and 0.5 µM in cultured aortic smooth muscle cells), but fails to inhibit binding to receptors in tissues in which $ET_B$ receptors predominate at concentrations up to 100 µM. Cyclic pentapeptides related to BE-18257B, such as cyclo(D-Asp-Pro-D-Val-Leu-D-Trp) (BQ-123), have been synthesized and shown to exhibit activity as $ET_A$ receptor antagonists (see, U.S. Pat. No. 5,114,918 to Ishikawa et al.; see, also, EP A1 0 436 189 to BANYU PHARMACEUTICAL CO., LTD (Oct. 7, 1991)). Studies that measure the inhibition by these cyclic peptides of endothelin-1 binding to endothelin-specific receptors indicate that these cyclic peptides bind preferentially to $ET_A$ receptors.

The analog [Ala$^{1,3,11,15}$]endothelin-1, in which the four Cys residues are replaced with Ala, inhibits $^{125}$I-endothelin-1 binding to cerebral membranes, in which $ET_B$ receptors predominate (Hiley et al. (1989) *Trends Pharmacol. Sci* 10: 47–49). This peptide and certain truncated forms of endothelin-1 elicit endothelium-dependent vasorelaxation of pre-contracted porcine pulmonary arteries to an extent that parallels the respective binding affinities of each form for $ET_B$ (Saeki et al. (1991) *Biochem. and Biophys Res. Commun.* 179: 286–292).

Endothelin antagonists and agonists as therapeutic agents

In view of the numerous physiological effects of endothelin and its apparent association with certain diseases, endothelin is believed to play a critical role in pathophysiological conditions, including hypertension, atherosclerosis, other vascular disorders, gastrointestinal disorders, renal failure, asthma, pulmonary hypertension, endotoxin shock, coronary vasospasm, cerebral vasospasm and others (see, e.g., Saito et al. (1990) *Hypertension* 15: 734–738; Tomita et al. (1989) *N. Engl. J. Med.* 321: 1127; Doherty (1992) *J. Med. Chem.* 35: 1493–1508; Morel et al. (1989) *Eur. J. Pharmacol.* 167: 427–428). Because endothelin is associated with these and other disease states, more detailed knowledge of the function and structure of the endothelin peptide family should provide insight in the progression and treatment of such conditions.

To aid in gaining this understanding, there is a need to identify compounds that modulate or alter endothelin activity. Compounds that modulate endothelin activity, particularly compounds that act as specific antagonists or agonists, may not only aid in elucidating the function of endothelin, but may be therapeutically useful. In particular, compounds that specifically interfere with the interaction of endothelin peptides with the $ET_A$, $ET_B$ or other receptors should may aid in the design of therapeutic agents, and may be useful as disease specific therapeutic agents.

Therefore, it is an object herein to provide compounds that have the ability to modulate the biological activity of one or more of the endothelin isopeptides. It is another object to provide compounds that have use as specific endothelin antagonists. It is also an object to use compounds that specifically interact with or inhibit the interaction of endothelin peptides with $ET_A$ or $ET_B$ receptors as therapeutic agents for the treatment of endothelin-mediated diseases and disorders.

SUMMARY OF THE INVENTION

Sulfonamides and methods for modulating the interaction of an endothelin peptide with $ET_A$ and/or $ET_B$ receptors are provided. In particular, sulfonamides and methods for inhibiting the binding of an endothelin peptide to $ET_A$ or $ET_B$ receptors. Sulfonamides and methods that act as endothelin peptide agonists with respect to $ET_A$ or $ET_B$ receptors are also provided.

The methods are effected by contacting the receptors with one or more sulfonamides prior to, simultaneously with, or subsequent to contacting the receptors with an endothelin peptide. The sulfonamides are substituted or unsubstituted monocyclic or polycyclic aromatic or heteroaromatic sulfonamides, such as benzene sulfonamides and naphthalene sulfonamides, and thiophene sulfonamides.

The sulfonamides have formula I:

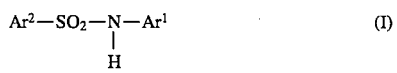

in which $Ar^1$ is a substituted or unsubstituted aryl group with one or more substituents, including an alkyl group, an aryl group, a substituted aryl group, a nitro group, an amino group or a halide or is an alkyl group. In particular, $Ar^1$ is alkly or is a five or six membered substituted or unsubstituted aromatic or heteroaromatic ring, including, 3- or 5-isoxazolyl, 2-thiazolyl, 2-pyrimidinyl, or substituted benzene groups, including aryloxy substituted benzene groups or is a bicyclic or tricyclic ring.

$Ar^1$ is, in certain embodiments, selected from groups such as:

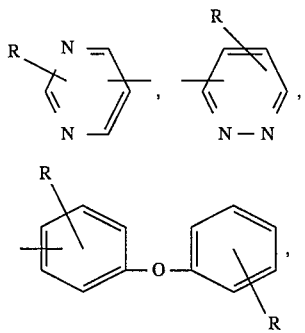

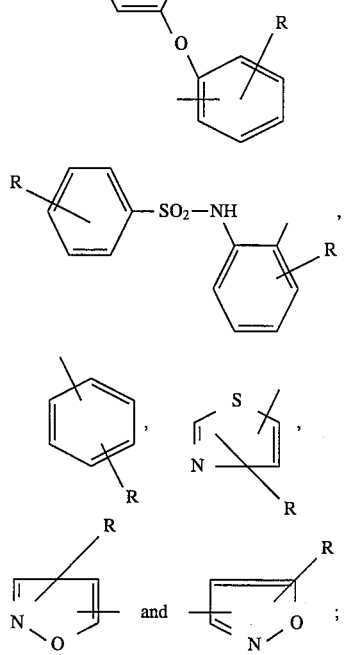

and R is selected from H, $NH_2$, halide, pseudohalide, alkyl alkylcarbonyl, formyl, an aromatic or heteroaromatic group, alkoxyalkyl, alkylamino, alkylthio, arylcarbonyl, aryloxy, arylamino, arylthio, haloalkyl, haloaryl, carbonyl, in which the aryl and alkyl portions, are unsubstituted or substituted with any of the preceding groups, and unsubstituted or substituted with any of the preceding groups, and straight or branched chains of from about 1 up to about 10–12 carbons, preferably, 1 to about 5 or 6 carbons. R is preferably H, $NH_2$, halide, $CH_3$, $CH_3O$ or another aromatic group. $Ar^2$ is any group such that the resulting sulfonamide inhibits binding by 50%, compared to binding in the absence of the sulfonamide, of an endothelin peptide to an endothelin receptor at a concentration of less than about 100 μM, except that $Ar^2$ is not phenyl or naphthyl when $Ar^1$ is N-(5-isoxazolyl) or N-(3-isoxazolyl) unless the isoxazole is a 4-halo-isoxazole.

$Ar^1$, in certain of these embodiments, has been selected from groups such as:

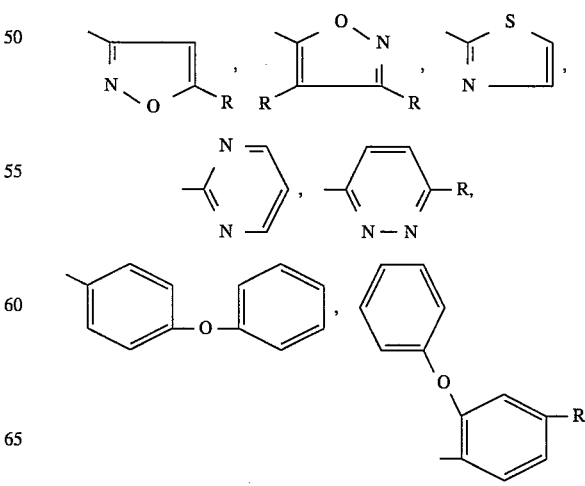

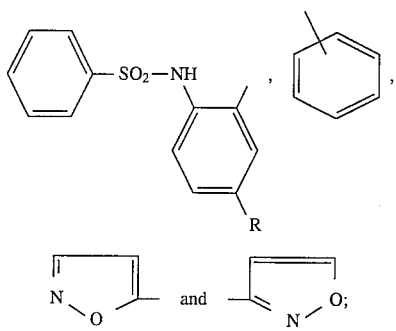

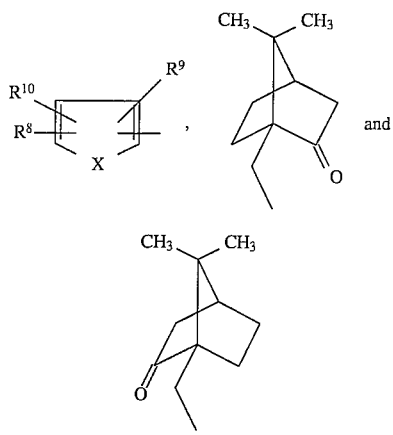

In the embodiments described in detail herein, $Ar^1$ is an isoxazole and the compounds are represented by the formulae II:

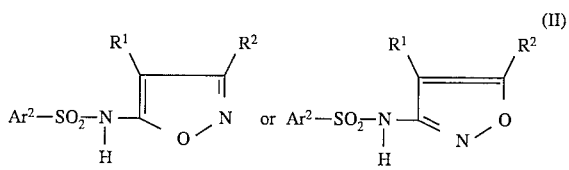
(II)

in which $R^1$ and $R^2$ are either (i), (ii) or (iii) as follows:

(i) $R^1$ and $R^2$ are each independently selected from H, $NH_2$, $NO_2$, halide, pseudohalide, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons; or, (ii) $R^1$ and $R^2$ together form $-(CH_2)_n-$, where n is 3 to 6; or, (iii) $R^1$ and $R^2$ together form 1,3-butadienyl, and with the proviso that $Ar^2$ is not phenyl or naphthyl unless $R^1$ is a halide.

Thus, $Ar^2$ is any group such that the resulting sulfonamide inhibits binding by 50%, compared to binding in the absence of the sulfonamide, of an endothelin peptide to an endothelin receptor at a concentration of less than about 100 µM, except that $Ar^2$ is not phenyl or naphthyl unless $R^1$ is a halide.

in particular, $Ar^2$ is alkyl, alkenyl, or is a group or isomer of a group selected from among groups, with the proviso that $Ar^2$ is not phenyl or naphthyl unless $R^1$ is a halide, such as:

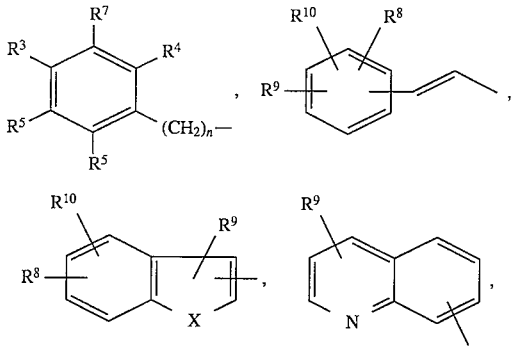

in which n is 0 to 10, preferably 0 to 6, more preferably 0 to 3, X is O, S, N or $NR^{11}$, where $R^{11}$, which is hydrogen or contains up to about 30 carbon atoms, generally 1 to 16 carbon atoms, is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0–2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; $R^{11}$ and $R^{15}$ are unsubstituted or are substituted with one or more substituents each selected independently from Z, which is hydrogen, halide, pseudoahlide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{11}$ and Z, is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl; each of $R^{11}$, $R^{12}$, $R^{15}$ and $R^{16}$ may be further substituted with the any of the groups set forth for Z;

$R^3$, $R^4$, $R^5$, $R^6$ and $R^7$ are each selected independently as from (i)–(iv) as follows:

(i) $R^3$, $R^4$, $R^5$, $R^6$ and $R^7$ are each selected independently from among H, NHOH, $NH_2$, $NO_2$, $N_3$, aminoalkyl, alkylamino, dialkylamino, carboxyl, carbonyl, hydroxyl, halide, pseudohalide, alkyl, alkenyl, alkynyl, aryl, heterocycle, alkoxy, alkylthio, alkyalkoxy, alkylsulfinyl, alkylsulfonyl, aryloxy, arylalkoxy, arylalkixy, arylamino, arylthio, arylsulfinyl, arylsulfonyl, haloalkyl, haloaryl, haloalkoxy, alkoxycarbonyl, alkylcarbonyl, arylcarbonyl, formyl, substituted or unsubstituted amido, substituted or unsubstituted ureido in which each of the preceding groups may be un substituted or substituted with groups such as H, $NH_2$, $NO_2$, alkyl, halide, and pseudohalide; or, alternatively, (ii) $R^4$ and $R^7$ together are substituted or unsubstituted 1,3-butadienyl, 1-chloro-1,3-butadienyl, 4-dimethylamino-1,3-butadienyl, 1-aza-1,3-butadienyl or 2-aza-1,3-butadienyl groups; and $R^3$, $R^5$ and $R^6$ are as defined in (i) above; or alternatively, (iii) $R^7$ and $R^3$ together are substituted or unsubstituted 1,3-butadienyl, 4-dimethylamino-1,3 butadienyl, 1-chloro-1,3-butadienyl, 1-aza-1,3-butadienyl or 2-aza-1,3-butadienyl groups; and n, X, $R^4$, $R^5$, $R^6$, $R^{11}$, $R^{12}$, $R^{15}$, $R^{16}$ and $R^{17}$ are as defined in (i) above; or alternatively, (iv) $R^3$, $R^5$, and $R^7$ are H; and $R^4$ and $R^6$ are each independently selected from alkyl, alkoxy, halide and aminoalkyl;

and $R^8$, $R^9$, $R^{10}$ are each independently selected as follows from (i) or (ii):

(i) $R^8$, $R^9$ and $R^{10}$, which each contain hydrogen or up to about 50 carbon atoms, generally up to about 30, more generally 20 or fewer, are each independently selected from hydrogen, halide pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, C(O)$R^{18}$, CO$_2R^{18}$, SH, S(O)$_nR^{18}$ in which n is 0–2, HNOH, NR$^{18}R^{19}$, NO$_2$, N$_3$, OR$^{18}$, R$^{19}$NCOR$^{18}$ and CONR$^{19}R^{18}$, in which $R^{19}$ is selected from hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, C(O)R$^{20}$, S(O)$_nR^{20}$ in which n is 0–2; and $R^{18}$ and $R^{20}$ are independently selected from hydrogen, alkyl, alkenyl, alkynyl, aryl, alkylaryl, heterocycle, alkoxy, aryloxy, aralkyl, aralkoxy, cycloalkyl, cycloalkenyl or cycloalkynyl; and any of the groups set forth for $R^8$, $R^9$ and $R^{10}$ are unsubstituted or substituted with any substituents set forth for Z, which is is hydrogen, halide, pseudoahlide, alkyl, alkoxy, alkenyl, alkynyl, aryl, aryloxy, heterocycle, aralkyl, aralkoxy, cycloalkyl, cycloalkenyl, cycloalkynyl, OH, CN, C(O)R$^{21}$, CO$_2R^{21}$, SH, S(O)$_nR^{21}$ in which n is 0–2, NHOH, NR$^{22}R^{21}$, NO$_2$, N$_3$, OR$^{21}$, R$^{22}$NCOR$^{21}$ and CONR$^{22}R^{21}$; $R^{22}$ is selected from hydrogen, alkyl, alkenyl, alkynyl, aryl, alkylaryl, heterocycle, aralkyl, alkoxy, aralkoxy, cycloalkyl, cycloalkenyl, cycloalkynyl, C(O)R$^{23}$ and S(O)$_nR^{23}$ in which n is 0–2; and $R^{21}$ and $R^{23}$ are independently selected from hydrogen, alkyl, alkenyl, alkynyl, aryl, alkylaryl, heterocycle, aralkyl, aralkoxy, cycloalkyl, cycloalkenyl or cycloalkynyl;

(ii) any two of $R^8$, $R^9$ and $R^{10}$ form an aryl, aromatic ring, heteroaromatic ring, alicyclic or heterocyclic ring, which is saturated or unsaturated, containing from about 3 to about 16 members, preferably 3 to about 10 members, more preferably 5 to 7 members that is unsubstituted or substituted with one or more substituents in each each substituent is independently selected from Z; and the other of $R^8$, $R^9$ and $R^{10}$ is selected as in (i).

In the above embodiments, the alkyl, alkyny and alkenyl portions of each listed substituent are straight or branched chains, acyclic or cyclic, and preferably have from about 1 up to about 10 carbons; in more preferred embodiments they have from 1–6 carbons, and they can have fewer than 6 carbons. The aryl, alicyclic, aromatic rings and heterocyclic groups can have from 3 to 16, generally, 3–7, more often 5–7 members in the rings, and may be single or fused rings. The ring size and carbon chain length are selected up to an amount that the resulting molecule binds to retains activity as an endothelin antagonist or agonist, such that the resulting compound inhibits binding by 50%, compared to binding in the absence of the sulfonamide, of an endothelin peptide to an endothelin receptor at a concentration of less than about 100 μM.

Thus, Ar$^2$ is a substituted or unsubstituted group selected from among groups such as the following: naphthyl, phenyl, biphenyl, quinolyl, styryl, thiophenyl, furyl, isoquinolyl, pyrrolyl, benzofuranyl, pyridinyl, thionaphthalyl, indolyl, alkyl, and alkenyl. It is understood that the positions indicated for substituents, including the sulfonamide groups, may be varied. Thus, for example, compounds herein encompass groups that include thiophene-3-sulfonamides and thiophene-2-sulfonamides.

In the embodiments described in detail herein, Ar$^2$ is thiophenyl, furyl, pyrrolyl or a group that is a derivative of or analog, as described below, of a thiophenyl, furyl, pyrroly group, Ar$^1$ is preferably N-(5-isoxazolyl) or N-(3-isoxazolyl), and the compounds are represented by the formulae III:

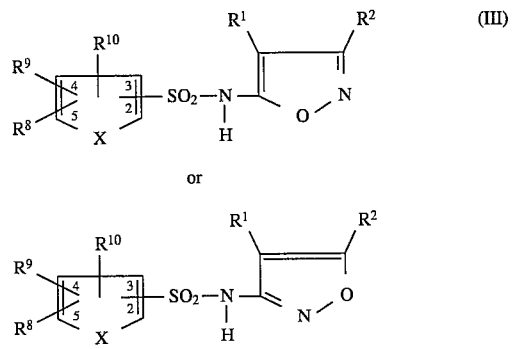

in which $R^1$, $R^2$, X, $R^8$, $R^9$ and $R^{10}$ are selected as defined above.

In preferred embodiments herein, $R^1$ and $R^2$ are selected independently from among alkyl, lower alkenyl, lower alkynl, lower haloalkyl, halide, pseudohalide or H; and Ar$^2$ is represented by the formulae IV:

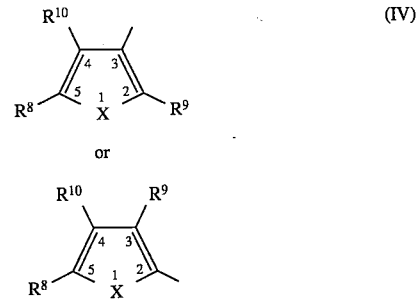

that can be substituted at any or all positions or is an analog of compounds of formula (IV) in which the substituents form fused aromatic, aliphatic or heterocyclic rings; and in which X is NR$^{11}$, O, or S, and $R^{11}$, which is hydrogen or contains up to about 30 carbon atoms, preferably 1 to 10, more preferably 1 to 6, and is selected as defined above. $R^8$, $R^9$, $R^{10}$ are selected as described above.

In certain preferred embodiments herein, $R^{11}$ is aryl, such as phenyl or alkyl phenyl, hydrogen or lower alkyl, and $R^8$, $R^9$, $R^{10}$ are independently selected from hydrogen, halide, lower alkyl, lower aryl, lower heterocycle, lower aralkyl C(O)$_2R^{18}$, CO$_2^{18}$, NO$_2$, OR$^{18}$SR$^{18}$NR$^{18}$COR$^{19}$ or CONR$^{19}R^{18}$; $R^{18}$ and $R^{19}$ are preferably hydrogen, lower alkyl, and lower aryl, and Z is hydrogen, halide, pseudohalide, lower alkyl, lower alkoxy or pseudohalo- or halo(lower)alkyl. In certain more preferred embodiments, $R^8$ and $R^{10}$ are hydrogen, halide or methyl, more preferably hydrogen or halide, and $R^9$ is selected independently from hydrogen, halide, aryl, pseudohalide and lower alkyl, preferably methyl or ethyl, COR$^{18}$, CONR$^{18}R^{19}$ and NR$^{18}$COR$^{19}$.

In the preferred compounds herein, $R^2$ i preferably, selected from among alkyl, lower alkenyl, lower alkynl, lower haloalkyl, halide or H; and $R^1$ is halide or lower alkyl, and more preferably, $R^1$ is bromide or chloride, methyl or ethyl. In the most active compounds provided herein, as evidenced by in vitro binding assays, $R^1$ is bromide or chloride.

Preferred compounds also include compounds that are $ET_B$ receptor selective or that bind to $ET_B$ receptors with an $IC_{50}$ of less than about 1 µM. In these compounds, $R^2$ is selected from among alkyl, lower alkenyl, lower alkynyl, lower haloalkyl, halide or H; and $R^1$ is halide or lower alkyl, and in preferred embodiments, $R^1$ is bromide or chloride; $R^9$ and $R^{10}$ are selected independently from hydrogen, lower alkyl, preferably methyl or ethyl, or halide, and $R^e$, which is the substituent at the 5-position (see,e.g., formulae III and IV), is aryl or a heterocycle, particularly phenyl and isoxazolyl, which are unsubstituted or substituted with Z, which is preferably lower alkyl or halide.

Of the compounds described herein, those that inhibit or increase an endothelin-mediated activity by about 50% at concentrations of less than about 10 µM are preferred. More preferred are those that inhibit or increase an endothelin-mediated activity by about 50% at concentrations of less than about 1 µM, more preferably less than about 0.1 µM, even more preferably less than about 0.01 µM, and most preferably less than about 0.005 µM.

Also among the most preferred compounds for use in methods provided herein, are those that are $ET_A$ selective, i.e., they interact with $ET_A$ receptors at concentrations at substantially lower concentratons (at an $IC_{50}$ at least about 10-fold lower, preferably 100-fold lower) than they interact with $ET_B$ receptors. Other preferred compounds are $ET_B$ selective. These compounds interact with $ET_B$ receptors at $IC_{50}$ concentrations that are at least about 10-fold lower than the concentrations at which they interact with $ET_A$ receptors. In particular, compounds that interact with $ET_A$ with an $IC_{50}$ of less than about 10 µM, preferably less than 1 µM, more preferably less than 0.1 µM, but with $ET_B$ with an $IC_{50}$ of greater than about about 10 µM or compounds that interact with $ET_B$ with an $IC_{50}$ of less than about 10 µM, preferably less than 1 µM, more preferably less than 0.1 µM, but with $ET_A$ with an $IC_{50}$ of greater than about 10 µM are preferred.

Among others of the preferred compounds for use in the methods herein are any compounds that interact with $ET_A$ and/or $ET_B$ receptors with an $IC_{50}$ of less than about 10 µM, more preferably less than 1 µM, even more preferably less than about 0.1 µM, even more preferably less than about 0.01 µM and most preferably less than about 0.005 µM.

Pharmaceutical compositions formulated for administration by an appropriate route and means containing effective concentrations of one or more of the compounds provided herein or pharmaceutically acceptable salts or acids thereof that deliver amounts effective for the treatment of hypertension, stroke, asthma, shock, ocular hypertension, glaucoma, renal failure, inadequate retinal perfusion and other conditions that are in some manner mediated by an endothelin peptide or that involve vasoconstriction or whose symptoms can be ameliorated by administration of an endothelin antagonist or agonist, are also provided. Particularly preferred compositions are those that deliver amounts effective for the treatment of hypertension or renal failure. The effective amounts and concentrations are effective for ameliorating any of the symptoms of any of the disorders.

Methods for treatment of endothelin-mediated disorders, including but not limited to, hypertension, asthma, shock, ocular hypertension, glaucoma, inadequate retinal perfusion and other conditions that are in some manner mediated by an endothelin peptide, or for treatment of disorder that involve vasoconstriction or that are ameliorated by administration of an endothelin antagonist or agonist are provided.

In particular, methods of treating endothelin-mediated disorders by administering effective amounts of the sulfonamides, prodrugs or other suitable derivatives of the sulfonamides are provided. In particular, methods for treating endothelin-mediated disorders, including hypertension, cardiovascular diseases, cardiac diseases including myocardial infarction, pulmonary hypertension, erythropoietin-mediated hypertension, respiratory diseases and inflammatory diseases, including asthma, bronchoconstriction, ophthalmologic diseases, gastroenteric diseases, renal failure, endotoxin shock, menstrual disorders, obstetric conditions, wounds, anaphylactic shock, hemorrhagic shock, and other diseases in which endothelin mediated physiological responses are implicated, by administering effective amounts of one or more of the compounds provided herein in pharmaceutically acceptable carriers are provided. Preferred methods of treatment are methods for treatment of hypertension and renal failure.

More preferred methods of treatment are those in which the compositions contain at least one compound that inhibits the interaction of endothelin-1 with $ET_A$ receptors at an $IC_{50}$ of less than about 10 µM, and preferably less than about 5 µM, more preferably less than about 1 µM, even more preferably less than 0.1 µM, and most preferably less than 0.05 µM Other preferred methods are those in which the compositions contain one or more compounds that is (are) $ET_A$ selective or one or more compounds that is (are) $ET_B$ selective. Methods in which the compounds are $ET_A$ selective are for treatment of disorders, such as hypertension; and methods in which the compounds are $ET_B$ selective are for treatment of disorders, such as asthma, that require bronchodilation.

In practicing the methods, effective amounts of compositions containing therapeutically effective concentrations of the compounds formulated for oral, intravenous, local and topical application for the treatment of hypertension, cardiovascular diseases, cardiac diseases, including myocardial infarction, respiratory diseases, including asthma, inflammatory diseases, ophthalmologic diseases, gastroenteric diseases, renal failure, immunosuppressant-mediated renal vasoconstriction, erythropoietin-mediated vasoconstriction, endotoxin shock, anaphylactic shock, hemorrhagic shock, pulmonary hypertension, and other diseases in which endothelin mediated physiological responses are implicated are administered to an individual exhibiting the symptoms of one or more of these disorders. The amounts are effective to ameliorate or eliminate one or more symptoms of the disorders.

Methods for the identification and isolation of endothelin receptor subtypes are also provided. In particular, methods for detecting, distinguishing and isolating endothelin receptors using the disclosed compounds are provided. In particular, methods are provided for detecting, distinguishing and isolating endothelin receptors using the compounds provided herein.

In addition, methods for identifying compounds that are suitable for use in treating particular diseases based on their preferential affinity for a particular endothelin receptor subtype are also provided.

Articles of manufacture containing packaging material, a compound provided herein, which is effective for ameliorating the symptoms of an endothelin-mediated disorder, antagonizing the effects of endothelin or inhibiting binding of an endothelin peptide to an ET receptor with an $IC_{50}$ of less than about 10 µM, within the packaging material, and a label that indicates that the compound or salt thereof is used for antagonizing the effects of endothelin, treating an endothelin-mediated disorder, or inhibiting the binding of an endothelin peptide to an ET receptor are provided.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference.

As used herein, endothelin (ET) peptides include peptides that have substantially the amino acid sequence of endothelin-1, endothelin-2 or endothelin-3 and that act as potent endogenous vasoconstrictor peptides.

As used herein, an endothelin-mediated condition is a condition that is caused by abnormal endothelin activity or one in which compounds that inhibit endothelin activity have therapeutic use. Such diseases include, but are not limited to hypertension, cardiovascular disease, asthma, inflammatory diseases, ophthalmologic disease, menstrual disorders, obstetric conditions, gastroenteric disease, renal failure, pulmonary hypertension, endotoxin shock, anaphylactic shock, or hemorrhagic shock. Endothelin-mediated conditions also include conditions that result from therapy with agents, such as erythropoietin and immunosuppressants, that elevate endothelin levels.

As used herein an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

As used herein, an endothelin agonist is a compound that potentiates or exhibits a biological activity associated with or possessed by an endothelin peptide.

As used herein, an endothelin antagonist is a compound, such as a drug or an antibody, that inhibits endothelin-stimulated vasoconstriction and contraction and other endothelin-mediated physiological responses. The antagonist may act by interfering with the interaction of the endothelin with an endothelin-specific receptor or by interfering with the physiological response to or bioactivity of an endothelin isopeptide, such as vasoconstriction. Thus, as used herein, an endothelin antagonist interferes with endothelin-stimulated vasoconstriction or other response or interferes with the interaction of an endothelin with an endothelin-specific receptor, such as $ET_A$ receptors, as assessed by assays known to those of skill in the art.

The effectiveness of potential agonists and antagonists can be assessed using methods known to those of skill in the art. For example, endothelin agonist activity can be identified by its ability to stimulate vasoconstriction of isolated rat thoracic aorta or portal vein ring segments (Borges et al. (1989) "Tissue selectivity of endothelin" *Eur. J. Pharmacol.* 165: 223–230). Endothelin antagonist activity can be assessed by the ability to interfere with endothelin-induced vasoconstriction.

As used herein, the biological activity or bioactivity of endothelin includes any activity induced, potentiated or influenced by endothelin in vivo. It also includes the ability to bind to particular receptors and to induce a functional response, such as vasoconstriction. It may be assessed by in vivo assays or by in vitro assays, such as those exemplified herein. The relevant activities include, but are not limited to, vasoconstriction, vasorelaxation and bronchodilation. For example, $ET_B$ receptors appear to be expressed in vascular endothelial cells and may mediate vasodilation and other such responses; whereas $ET_A$ receptors, which are endothelin-1-specific, occur on smooth muscle and are linked to vasoconstriction Any assay known to those of skill in the art to measure or detect such activity may be used to assess such activity (see, e.g., Spokes et al. (1989) *J. Cardiovasc. Pharmacol.* 13(Suppl. 5):S191–S192; Spinella et al. (1991) *Proc. Natl. Acad. Sci. USA* 88: 7443–7446; Cardell et al. (1991) *Neurochem. Int.* 18:571–574); and the Examples herein).

As used herein, the $IC_{50}$ refers to an amount, concentration or dosage of a particular test compound that achieves a 50% inhibition of a maximal response, such as binding of endothelin to tissue receptors, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein a sulfonamide that is $ET_A$ selective refers to sulfonamides that exhibit an $IC_{50}$ that is at least about 10-fold lower with respect to $ET_A$ receptors than $ET_B$ receptors.

As used herein, a sulfonamide that is $ET_B$ selective refers to sulfonamides that exhibit an $IC_{50}$ that is at least about 10-fold lower with respect to $ET_B$ receptors than $ET_A$ receptors.

As used herein, pharmaceutically acceptable salts, esters or other derivatives of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxy groups can be esterified or etherified.

As used herein, treatment means any manner in which the symptoms of a conditions, disorder or disease are ameliorated or otherwise beneficially altered. Treatment also encompasses any pharmaceutical use of the compositions herein, such as use as contraceptive agents.

As used herein, amelioration of the symptoms of a particular disorder by administration of a particular pharmaceutical composition refers to any lessening, whether permanent or temporary, lasting or transient that can be attributed to or associated with administration of the composition.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388–392). For example, succinylsulfathiazole is a prodrug of 4-amino-N-(2-thiazoyl)benzene-sulfonamide (sulfathiazole) that exhibits altered transport characteristics.

As used herein, "halogen" or "halide" refers to F, Cl, Br or I.

As used herein, pseudohalides are compounds that behave substantially similar to halides. Such compounds can be used in the same manner and treated in the same manner as halides ($X^-$, in which X is a halogen, such as Cl or Br). Pseudohalides include, but are not limited to cyanide, cyanate, thiocyanate, selenocyanate and azide.

As used herein, lower alkyl, lower alkenyl, and lower alkynyl refer to carbon chains having less than about 6 carbons. In preferred embodiments of the compounds provided herein that include alkyl, alkenyl, or alkynyl portions include lower alkyl, lower alkenyl, and lower alkynyl portions.

As used herein aryl refers to cyclic groups containing from 3 to 15 or 16 carbon atoms, preferably from 5 to 10. Aryl groups include, but are not limited to groups, such as phenyl, substituted phenyl, napthyl, substituted naphthyl, in which the substitunent is lower alkyl, halogen, or lower alkoxy. Preferred aryl groups are lower aryl groups that contain less than 7 carbons in the ring structure.

As used herein, the nomenclature alkyl, alkoxy, carbonyl, etc. are used as is generally understood by those of skill in this art. For example, as used herein alkyl refers to saturated carbon chains that contain one or more carbons; the chains may be straight or branched or include cyclic portions or be cyclic. As used herein, alicyclic refers to aryl groups that are cyclic.

As used herein, "haloalkyl" refers to a lower alkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO— in which R is a haloalkyl group.

As used herein, "aminocarbonyl" refers to —C(O)NH$_2$.

As used herein, "alkylaminocarbonyl" refers to —C(O)NHR in which R is hydrogen, alkyl, preferably lower alkyl or aryl, preferably lower aryl.

As used herein "dialkylaminocarbonyl" as used herein refers to —C(O)NR'R in which R' and R are independently selected from alkyl or aryl, preferably lower alkyl or lower aryl; "carboxamide" refers to groups of formula NR'COR.

As used herein, "alkoxycarbonyl" as used herein refers to —C(O)OR in which R is alkyl, preferably lower alkyl or aryl, preferably lower aryl.

As used herein, "alkoxy" and "thioalkoxy" refer to RO— and RS—, in which R is alkyl, preferably lower alkyl or aryl, preferably lower aryl.

As used herein, "haloalkoxy" refers to RO— in which R is a haloalkyl group.

As used herein, "aminocarbonyl" refers to —C(O)NH$_2$.

As used herein, "alkylaminocarbonyl" refers to —C(O)NHR in which R is alkyl, preferably lower alkyl or aryl, preferably lower aryl.

As used herein, "alkoxycarbonyl" refers to —C(O)OR in which R is alkyl, preferably lower alkyl.

As used herein, cycloalkyl refers to satured cyclic carbon chains; cycloalkyenyl and cycloalkynyl refer to cyclic carbon chains that include at least one unsaturated triple bond. The cyclic portions of the carbon chains may include one ring or two or more fused rings.

As used herein, heterocycle or heteroaryl refers to ring structures that include at least one carbon atom and one or more atoms, such as N, S and O. The rings may be single rings or two or more fused rings. Heteroaryl is used interchangeably with heterocycle.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942–944).

A. Compounds for use in treating endothelin-mediated diseases

Compounds and methods for treating endothelin-mediated diseases using the compounds of formula I are provided. In particular, the compounds provided herein have formulae II. The more preferred compounds of formulae I and and II provided herein are compounds in which $Ar^1$ is N-(5-isoxazolyl) or N-(3-isoxazolyl) that can be represented by the formulae V:

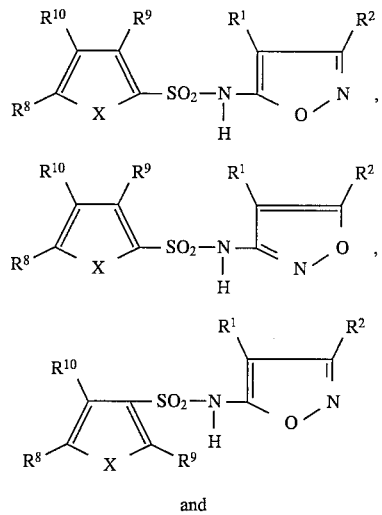

and

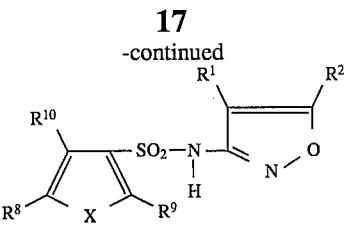

in which:

$R^1$ and $R^2$ are either (i), (ii) or (iii) as follows:

(i) $R^1$ and $R^2$ are each independently selected from H, $NH_2$, $NO_2$, halide, pseudohalide, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons; or, (ii) $R^1$ and $R^2$ together form $—(CH_2)_n—$, where n is 3 to 6; or, (iii) $R^1$ and $R^2$ together form 1,3-butadienyl;

X is O, S, NH or $NR^{11}$ in which $R^{11}$, which contains up to about 30–50 atoms, generally 1 to 20 atoms, and which is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$, $S(O)_nR^{15}$ in which n is 0–2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; m is 0–2; $R^{11}$ and $R^{15}$, are unsubstituted or are substituted with one or more substituents each independently selected from Z, which is hydrogen, halide, pseudoahlide, alkyl, alkoxy, alkenyl, alkynyl, aryl, heterocycle, aralkyl, aralkoxy, cycloalkyl cycloalkenyl cycloalkynyl, OH CN, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{11}$ and Z, is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$ and $R^{16}$ may be further substituted with substituents selected from Z;

and $R^8$, $R^9$, $R^{10}$, which each, when not hydrogen, contain up to about 30 carbon atoms or more, generally fewer than about 16, are each independently selected as follows from (i) or (ii):

(i) $R^8$, $R^9$ and $R^{10}$ are each independently selected from hydrogen, halide pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{18}$, $CO_2R^{18}$, SH, $S(O)_nR^{18}$ in which n is 0–2, HNOH $NR^{18}R^{19}$, $NO_2$, $N_3$, $OR^{18}$, $R^{19}NCOR^{18}$ and $CONR^{19}R^{18}$, in which $R^{19}$ is selected from hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, $C(O)R^{20}$, $S(O)_nR^{20}$ in which n is 0–2; and $R^{18}$ and $R^{20}$ are independently selected from hydrogen, alkyl, alkenyl, alkynyl, aryl, alkylaryl, heterocycle, alkoxy, aryloxy, aralkyl, aralkoxy, cycloalkyl, cycloalkenyl or cycloalkynyl, which is hydrogen, halide, pseudoahlide, alkyl, alkoxy, alkenyl, alkynyl, aryl, aryloxy, heterocycle, aralkyl, aralkoxy, cycloalkyl, cycloalkenyl, cycloalkynyl; and any of the groups set forth for $R^8$, $R^9$ and $R^{10}$ are unsubstituted or substituted with any substituents set forth for Z, which is is hydrogen, halide, pseudoahlide, alkyl, alkoxy, alkenyl, alkynyl, aryl, aryloxy, heterocycle, aralkyl, aralkoxy, cycloalkyl, cycloalkenyl, cycloalkynyl, OH CN, $C(O)R^{21}$, $CO_2$, $R^{21}$, SH $S(O)_nR^{21}$ in which n is 0–2, NHOH, $NR^{22}R^{21}$, $NO_2$, $N_3$, $OR^{21}$, $R^{22}NCOR^{21}$ and $CONR^{22}R^{21}$; $R^{22}$ is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{23}$ and $S(O)_nR^{23}$ in which n is 0–2; and $R^{21}$ and $R^{23}$ are independently selected from hydrogen, alkyl, alkenyl, alkynyl, aryl, alkylaryl, heterocycle, aralkyl, aralkoxy, cycloalkyl, cycloalkenyl and cycloalkynyl, $C(O)R^{25}$ and $S(O)_nR^{25}$ in which n is 0–2; $R^{24}$ is hydrogen, alkyl, alkenyl, alkynyl, aryl, alkylaryl, heterocycle, aralkyl, aralkoxy, cycloalkyl, cycloalkenyl or cycloalkynyl; and $R^{25}$ is hydrogen, alkyl, alkenyl, alkynyl, aryl, alkylaryl, heterocycle, aralkyl, aralkoxy, cycloalkyl, cycloalkenyl or cycloalkynyl; any of the preceding groups, including $R^8$, $R^9$, $R^{10}$, $R^{18}$, $R^{19}$, $R^{20}$, $R^{21}$, $R^{22}$, $R^{23}$, $R^{24}$ and $R^{25}$ may be unsubstituted, except as specified, or may be further substituted with substituents selected from Z, which is is hydrogen, halide, pseudoahlide, alkyl, alkoxy, alkenyl, alkynyl, aryl, aryloxy, heterocycle, aralkyl, aralkoxy, cycloalkyl, cycloalkenyl, cycloalkynyl; or (ii) any two of $R^8$, $R^9$ and $R^{10}$ form an aromatic or heteroaromatic ring or an alicyclic or heterocyclic ring, which is saturated or unsaturated, containing from about 3 to about 16 members, preferably 3 to about 10 members, more preferably 5 to 7 members, and which is unsubstituted or substituted with one or more substituents in each substituent is independently selected from Z; and the other of $R^8$, $R^9$ and $R^{10}$ is selected as in (i).

In the above embodiments, the alkyl, alkyny and alkenyl portions are straight or branched chains, acyclic or cyclic, and have from about 1 up to about 10 carbons; in certain of the more preferred embodiments they have from 1–6 carbons, and they can have fewer than 6 carbons. The aryl, homocyclic and heterocyclic groups can have from 3 to 16, generally, 3–7, more often 5–7 members in the rings, and may be single or fused rings. The ring size and carbon chain length are selected such that the resulting molecule binds to exhibits activity as an endothelin antagonist or agonist as evidenced by in vitro or in vivo tests, particularly the tests exemplified herein.

In preferred embodiments: X is S, O, $NR^{11}$ in which $R^{11}$ is aryl, hydrogen, or lower alkyl, preferably, a substituted or unsubstituted aryl, particularly phenyl, preferably unsubstituted or substituted with lower alkyl or halogen hydrogen or lower alkyl; $R^1$ is hydrogen, halide, pseudohalide, lower alkyl or lower haloalkyl, most preferably halide; $R^2$ is hydrogen, lower alkyl or lower haloalkyl; and $R^8$, $R^9$ and $R^{10}$ are each selected independently from from hydrogen, halide, pseudohalide, lower alkyl, lower aryl, lower heterocycle, lower aralkyl, $S(O)_nR^{18}$ in which n is 0–2, $C(O)R^{18}$, $CO_2R^{18}$, $NO_2$, $OR^{18}$ or $CONR^{19}R^{19}$; $R^{19}$ is preferably hydrogen, lower alkyl, and lower aryl, $C(O)R^{20}$, $S(O)_nR^{20}$ in which n is 0–2; $R^{18}$ is preferably hydrogen, halide, lower alkyl or lower aryl, and $R^{20}$ is preferably hydrogen, halide or lower alkyl; and Z is hydrogen, halide, pseudohalide, lower alkyl or lower pseudohaloalkyl or lower haloalkyl. In particular, at least one of $R^8$, $R^9$ and $R^{10}$ is selected from methyl, phenyl, pyrazolyl, isoxazolyl, carbomethoxy, carboxamide, halide, hydrogen, isopropylphenyl, pyridyl, carboxyl, phenyl, phenylcarboxamide, benzenesulfonyl, loweralkylphenylcarboxamide, biphenylcarboxamide, (lower)alkyloxyphenylcarboxamide and halophenylcarboxamide and, preferably, two of $R^8$, $R^9$ and $R^{10}$ are hydrogen, halide or lower alkyl. In more preferred of these embodiments X is S.

In more preferred embodiments, two of $R^8$, $R^9$ and $R^{10}$ are hydrogen, halide or lower alkyl and the other is hydrogen, halide, pseudohalide, lower alkyl, lower aryl, heterolower aryl, lower aralkyl, $C(O)R^{18}$, $CO_2$, $R^{18}$, $NO_2$, $OR^{18}$ or $CONR^{19}R^{18}$. In yet more preferred embodiments $R^{19}$ is phenyl and $R^{18}$ is hydrogen, halide or lower alkyl. In more preferred of these embodiments, two of $R^8$, $R^9$ and $R^{10}$ are hydrogen or lower alkyl and the other is halide, lower alkyl, $C(O)R^{18}$, $CO_2R^{18}$, $NO_2$, $OR^{18}$ or $CONR^{19}R^{18}$; $R^{18}$ is hydrogen or lower alkyl. In all embodiments, $R^1$ is preferably halide, H, $CH_3$ or $C_2H_5$, and $R^2$ is H, $CH_3$, $C_2H_5$, $C_2F_5$ or $CF_3$. In yet more preferred embodiments, $R^1$ preferably Br or Cl; $R^2$ is H, $CH_3$, $C_2H_5$, or $CF_3$.

In certain preferred embodiments, $R^8$ and $R^{10}$ are H, halide or lower alkyl; and $R^9$ is any of the above listed substituents, and particularly, when a potent $ET_A$ antagonist is desired is a substituted carboxamide. In other preferred embodiments it is preferred that $R^9$ and $R^{10}$ are H or lower alkyl and $R^8$ is any of the above-listed substituents. In the preferred of these embodiments, $R^1$ is halide, H, $CH_3$ or $C_2H_5$, and $R^2$ is H, $CH_3$, $C_2H_5$, $C_2F_5$ or $CF_3$. In yet more preferred embodiments, $R^1$ is Br or Cl; and $R^2$ is H, $CH_3$, $C_2H_5$, or $CF_3$.

In embodiments in which $ET_B$ antagonists are desired, it is preferred that $R^9$ and $R^{10}$ are H or lower alkyl and $R^8$ is a heterocyclic or aromatic ring of preferably from 3 to 14, more preferably, 5 to 7, members in the ring. In particular, if X is S, $R^9$ and $R^{10}$ are H or lower alkyl, and $R^8$, is aryl, particularly unsubstituted or substituted phenyl, such as 4-ethylphenyl. If X is N, then $R^{11}$ is aryl, particularly unsubstituted phenyl or substituted phenyl, such as isopropylphenyl and $R^8$, $R^9$ and $R^{10}$ are preferably H, halide or lower alkyl.

In all embodiments, $R^1$ is preferably halide or lower alkyl, most preferably Br, and the compounds are, with reference to formulae IV, 2- or 3-sulfonamides, particularly thiophene sulfonamides.

The most preferred compounds provided herein have an $IC_{50}$ for $ET_A$ receptors in the assays exemplified herein between about 0.005 µM and 0.1 µM. These compounds include: N-(4-bromo-3-methyl-5-isoxazolyl)-2-(N-phenylcarboxamide)thiophene-3-sulfonamide; N-(3,4-dimethyl-5-isoxazolyl)-2-( N-phenylcarboxamide)thiophene-3-sulfonamide; N-(4-bromo-3-methyl-5-isoxazolyl)-2,5-dimethylthiophene-3-sulfonamide; N-(4-bromo-3-methyl-5-isoxazolyl)-2-(carbomethoxy)thiophene-3-sulfonamide; N-(4-bromo-3-methyl-5-isoxazolyl)thiophene-2-sulfonamide; N-(4-bromo-3-methyl-5-isoxazolyl)-2-[N-( 4-biphenyl)carboxamide]thiophene- 3-sulfonamide; N-(4-bromo-3-methyl-5-isoxazolyl)-2-[N-(4-ethylphenyl)carboxamide]thiophene-3-sulfonamide; N-(4-bromo-3-methyl-5-isoxazolyl)-2-[N-(benzylcarboxamide]thiophene-3-sulfonamide; N-(4-bromo-3-methyl-5-isoxazolyl)-2-[N-(2-methoxyphenyl)carboxamide]thiophene-3-sulfonamide; N-(4-bromo-3-methyl-5-isoxazolyl)-2-[N-(3-methoxyphenyl)carboxamide]thiophene-3-sulfonamide; N-(4-bromo-3-methyl-5-isoxazolyl)-2-[N-(4-methoxyphenyl)carboxamide]thiophene-3-sulfonamide.

Other preferred compounds include those that have an $IC_{50}$ for $ET_B$ receptors, as measured in the assays herein, of between about 0.05 µM and 1 µM. These include compounds, such as, N-(4-bromo-3-methyl-5-isoxazolyl)-5-benzenesulfonylthiophene-2-sulfonamide, N-(4-bromo-3-methyl-5-isoxazolyl)-1-(4'-isopropylphenyl)pyrrole-2-sulfonamide; N-(4-bromo-3-methyl-5-isoxazolyl)-1-(4'-isopropylphenyl)pyrrole-3-sulfonamide; N-(4-bromo-3-methyl-5-isoxazolyl)-2-{3-[1-methyl-5-(trifluoromethyl)pyrazolyl]}thiophene-5-sulfonamide; N-(4-bromo-3-methyl-5-isoxazolyl)-2-[N-(4-biphenyl)carboxamide]thiophene-3-sulfonamide; N-(4-bromo-3-methyl-5-isoxazolyl)-2-[N-(4-ethylphenyl)carboxamide]thiophene-3-sulfonamide; N-(4-bromo-3-methyl-5-isoxazolyl)-5-thienylthiophene-2-sulfonamide; and N-(4-bromo-3-methyl-5-isoxazolyl)-5-(4-ethylphenyl)thiophene-2-sulfonamide.

The preparation of the above and other compounds that possess the requisite acitivities are set forth in the Examples.
B. Preparation of the compounds The compounds, in the methods herein may be prepared by reacting an appropiate sulfonyl chloride with 5-aminoisoxazoles substituted at the 3 and 4 positions, such as 5-amino-4-bromo-3-methylisoxazole, in tetrahydrofuran (THF) solution containing a base, such as sodium hydride. Following the reaction, the THF is removed under reduced pressure, the residue dissolved in water, acidified and extracted with methylene chloride. The organic layer is washed and then dried over anhydrous magnesium sulfate, the solvents are evaporated and the residue is purified by recrystallization using hexanes/ethylacetate to yield pure product.

Alternatively, the sulfonamides can be prepared from the corresponding sulfonyl chloride and the aminoisoxazole in pyridine with or without a catalytic amount of 4-dimethylaminopyridine (DMAP). In some cases, the bis-sulfonyl compound is obtained as the major or exclusive product. The bis-sulfonated products can be readily hydrolyzed to the sulfonamide using aqueous sodium hydroxide and a suitable co-solvent, such as methanol or tetrahydrofuran, generally at room temperature.

The sulfonylchlorides and derivatives may be prepared as known to those of skill in this art (see, e.g., U.S. Pat. Nos. 4,659,369, 4,861,366 and 4,753,672). Exemplary preparations of numerous compounds herein are set forth in the Examples.

Prodrugs and other derivatives of the compounds suitable for administration to humans may also be designed and prepared by methods known to those of skill in the art (see, e.g., Nogrady (1985) *Medicinal Chemistry A Biochemical Approach*, Oxford University Press, New York, pages 388–392.

The above-listed preferred compounds and others have been synthesized. Nuclear magnetic resonance spectroscopic (NMR), mass spectrometric, infrared spectroscopic and high performance liquid chromatographic analyses indicate that the synthesized compounds have structures consistent with those expected for such compounds and are at least about 98% pure.
C. Evaluation of the bioastivity of the compounds Standard physiological, pharmacological and biochemical procedures are available for testing the compounds to identify those that possess any biological activities of an endothelin peptide or the ability to interfere with or inhibit endothelin peptides. Compounds that exhibit in vitro activities, such as the ability to bind to endothelin receptors or to compete with one or more of the endothelin peptides for binding to endothelin receptors can be used in the methods for isolation of endothelin receptors and the methods for distinguishing the specificities of endothelin receptors, and are candidates for use in the methods of treating endothelin-mediated disorders.

Thus, other preferred compounds of formulas I and II, in addition to those of specifically identified herein, that are endothelin antagonists or agonists may be identified using such screening assays.

1. Identifying compounds that modulate the activity of an endothelin peptide

The compounds are tested for the ability to modulate the activity of endothelin-1. Numerous assays are known to those of skill in the art for evaluating the ability of compounds to modulate the activity of endothelin (see, e.g., U.S. Pat. No. 5,114,91 8 to Ishikawa et al.; EP A1 0 436 189 to BANYU PHARMACEUTICAL CO., LTD. (Oct. 7, 1991); Borges et al. (1989) *Eur. J. Pharm.* 165: 223–230; Filep et al. (1991) *Biochem. Biophys. Res. Commun.* 177: 171–176). In vitro studies may be corroborated with in vivo studies (see, e.g., U.S. Pat. No. 5,114,918 to Ishikawa et al.; EP A1 0 436 189 to BANYU PHARMACEUTICAL CO., LTD. (Oct. 7, 1991)) and pharmaceutical activity thereby evaluated. Such assays are described in the Examples herein and include the ability to compete for binding to $ET_A$ and $ET_B$ receptors present on membranes isolated from cell lines that have been genetically engineered to express either $ET_A$ or $ET_B$ receptors on their cell surfaces.

The properties of a potential antagonist may be assessed as a function of its ability to inhibit an endothelin induced activity in vitro using a particular tissue, such as rat portal vein and aorta as well as rat uterus, trachea and vas deferens (see e.g., Borges, R., Von Grafenstein, H. and Knight, D. E., Tissue selectivity of endothelin, *Eur. J. Pharmacol* 165:223–230, (1989)). The ability to act as an endothelin antagonist in vivo can be tested in hypertensive rats, ddy mice or other recognized animal models (see, Kaltenbronn et al. (1990) *J. Med. Chem.* 33:838–845, see, also, U.S. Pat. No. 5,114,918 to Ishikawa et al.; and EP A1 0 436 189 to BANYU PHARMACEUTICAL CO., LTD (Oct. 7, 1991); see, also Bolger et al. (1983) *J. Pharmacol. Exp. Ther.* 225291–309). Using the results of such animal studies, pharmaceutical effectiveness may be evaluated and pharmaceutically effective dosages determined. A potential agonist may also be evaluated using in vitro and in vivo assays known to those of skill in the art.

Endothelin activity can be identified by the ability of a test compound to stimulate constriction of isolated rat thoracic aorta (Borges et al. (1989) "Tissue selectivity of endothelin" *Eur. J. Pharmacol.* 165: 223–230). To perform the assay, the endothelium is abraded and ring segments mounted under tension in a tissue bath and treated with endothelin in the presence of the test compound. Changes in endothelin induced tension are recorded. Dose response curves may be generated and used to provide information regarding the relative inhibitory potency of the test compound. Other tissues, including heart, skeletal muscle, kidney, uterus, trachea and vas deferens, may be used for evaluating the effects of a particular test compound on tissue contraction.

Endothelin isotype specific antagonists may be identified by the ability of a test compound to interfere with endothelin binding to different tissues or cells expressing different endothelin-receptor subtypes, or to interfere with the biological effects of endothelin or an endothelin isotype (Takayanagi et al. (1991) *Reg. Pep.* 32: 23–37, Panek et al. (1992) *Biochem. Biophys. Res. Commun.* 183: 566–571 ). For example, $ET_B$ receptors are expressed in vascular endothelial cells, possibly mediating the release of prostacyclin and endothelium-derived relaxing factor (De Nucci et al. (1988) *Proc. Natl. Acad. Sci. USA* 85:9797). $ET_A$ receptors are not detected in cultured endothelial cells, which express $ET_B$ receptors.

The binding of compounds or inhibition of binding of endothelin to $ET_B$ receptors can be assessed by measuring the inhibition of endothelin-1-mediated release of prostacyclin, as measured by its major stable metabolite, 6-keto $PGF_{1\alpha}$, from cultured bovine aortic endothelial cells (see, e.g., Filep et al. (1991) *Biochem. and Biophys Res. Commun.* 177: 171–176). Thus, the relative affinity of the compounds for different endothelin receptors may be evaluated by determining the inhibitory dose response curves using tissues that differ in receptor subtype.

Using such assays, the relative affinities of the compounds for $ET_A$ receptors and $ET_B$ receptors have been and can be assessed. Those that possess the desired properties, such as specific inhibition of binding of endothelin-1, are selected. The selected compounds that exhibit desirable activities may be therapeutically useful and are tested for such uses using the above-described assays from which in vivo effectiveness may be evaluated (see, e.g., U.S. Pat. Nos. 5,248,807; 5,240,910; 5,198,548; 5,187,195; 5,082,838; 5,230,999; published Canadian Application Nos. 2,067,288 and 2071193; published Great Britain Application No. 2,259,450; Published International PCT Application No. WO 93/08799; Benigi et al. (1993) *Kidney International* 44:440–444; and Nirei et al. (1993) *Life Sciences* 52:1869–1874). Compounds that exhibit in vitro activities that correlate with in vivo effectiveness will then be formulated in suitable pharmaceutical compositions and used as therapeutics.

The compounds also may be used in methods for identifying and isolating endothelin-specific receptors and aiding in the design of compounds that are more potent endothelin antagonists or agonists or that are more specific for a particular endothelin receptor.

2. Isolation of endothelin receptors

A method for identifying endothelin receptors is provided. In practicing this method, one or more of the compounds is linked to a support and used in methods of affinity purification of receptors. By selecting compounds with particular specificities, distinct subclasses of ET receptors may be identified.

One or more of the compounds may be linked to an appropriate resin, such as Affi-gel, covalently or by other linkage, by methods known to those of skill in the art for linking endothelin to such resins (see, Schvartz et al. (1990) *Endocrinology* 126: 3218–3222). The linked compounds can be those that are specific for $ET_A$ or $ET_B$ receptors or other subclass of receptors.

The resin is pre-equilibrated with a suitable buffer generally at a physiological pH (7 to 8). A composition containing solubilized receptors from a selected tissue are mixed with the resin to which the compound is linked and the receptors are selectively eluted. The receptors can be identified by testing them for binding to an endothelin isopeptide or analog or by other methods by which proteins are identified and characterized. Preparation of the receptors, the resin and the elution method may be performed by modification of standard protocols known to those of skill in the art (see, e.g., Schvartz et al. (1990) *Endocrinology* 126: 3218–3222).

Other methods for distinguishing receptor type based on differential affinity to any of the compounds herein are provided. Any of the assays described herein for measuring the affinity of selected compounds for endothelin receptors may also be used to distinguish receptors subtypes based on affinity for particular compounds provided herein. In particular, an unknown receptor may be identified as an $ET_A$ or $ET_B$ receptor by measuring the binding affinity of the unknown receptor for a compound provided herein that has a known affinity for one receptor over the other. Such preferential interaction is useful for determining the particular disease that may be treated with a compound prepared as described herein. For example, compounds with high affinity for $ET_A$ receptors and little or no affinity for $ET_B$ receptors are candidates for use as hypertensive agents; whereas, compounds that preferentially interact with $ET_B$ receptors are candidates for use as anti-asthma agents.

D. Formulation and administration of the compositions

Effective concentrations of one or more of the sulfonamide compounds of formula I or II or pharmaceutically acceptable salts, esters or other derivatives thereof are mixed with a suitable pharmaceutical carrier or vehicle.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as tween, or dissolution in aqueous sodium bicarbonate. Derivatives of the compounds, such as salts of the compounds or prodrugs of the compounds may also be used in formulating effective pharmaceutical compositions.

The concentrations or the compounds are effective for delivery of an amount, upon administration, that ameliorates the symptoms of the endothelin-mediated disease. Typically, the compositions are formulated for single dosage administration.

Upon mixing or addition of the sulfonamide compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

Pharmaceutical carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients.

The active compounds can be administered by any appropriate route, for example, orally, parenterally, intravenously, intradermally, subcutaneously, or topically, in liquid, semi-liquid or solid form and are formulated in a manner suitable for each route of administration. Preferred modes of administration include oral and parenteral modes of administration.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems (see, e.g., U.S. Pat. No. 5,114,918 to Ishikawa et al.; EP A1 0 436 189 to BANYU PHARMACEUTICAL CO., LTD (Oct. 7, 1991); Borges et al. (1989) *Eur. J. Pharm.* 165: 223–230;: Filep et al. (1991) *Biochem. Biophys. Res. Commun.* 177: 171–176) and then extrapolated therefrom for dosages for humans.

The concentration of active compound in the drug composition will depend on absorption, inactivation and excretion rates of the active compound, the dosage schedule, and amount administered as well as other factors known to those of skill in the art. For example, the amount that is delivered is sufficient to treat the symptoms of hypertension. The effective amounts for treating endothelin-mediated disorders are expected to be higher than the amount of the sulfonamide compound that would be administered for treating bacterial infections.

Typically a therapeutically effective dosage should produce a serum concentration of active ingredient of from about 0. 1 ng/ml to about 50–1 µg/ml. The pharmaceutical compositions typically should provide a dosage of from about 0.01 mg to about 2000 mg of compound per kilogram of body weight per day. The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. For example, if the compound is used for treating asthma or hypertension, it may be used with other bronchodilators and antihypertensive agents, respectively.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parental preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compounds may be prepared with carriers that protect the compound against rapid elimination from the body, such as time release formulations or coatings. Such carriers include controlled release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of such formulations are known to those skilled in the art.

The compounds may be formulated for local or topical application, such as for topical application to the skin and mucous membranes, such as in the eye, in the form of gels, creams, and lotions and for application to the eye or for intracisternal or intraspinal application. Such solutions, particularly those intended for ophthalmic use, may be formulated as 0.01%–10% isotonic solutions, pH about 5–7, with appropriate salts. The compounds may be formulated as aeorsols for topical application, such as by inhalation (see, e.g., U.S. Pat. Nos. 4,044,126, 4,414,209, and 4,364,923, which describe aerosols for delivery of asteroid useful for treatment inflammatory diseases, particularly asthma).

Finally, the compounds may be packaged as articles of manufacture containing packaging material, a compound provided herein, which is effective for antagonizing the effects of endothelin, ameliorating the symptoms of an endothelin-mediated disorder, or inhibiting binding of an endothelin peptide to an ET receptor with an $IC_{50}$ of less than about 10 µM, within the packaging material, and a label that indicates that the compound or salt thereof is used for antagonizing the effects of endothelin, treating endothelin-mediated disorders or inhibiting the binding of an endothelin peptide to an ET receptor.

The following examples are included for illustrative purposes only and are not intended to limit the scope of the invention.

EXAMPLE 1

N-(4-Bromo-3-methyl-5-isoxazolyl)thiophene-2-sulfonamide

A solution of 5-amino-4-bromo-3-methylisoxazole (177 mg, 1.0 mmol) in dry tetrahydrofuran (THF, 2 ml) was added to a suspension of sodium hydride (60% dispersion in mineral oil, 90 mg, 2.2 mmol) in dry THF (1 ml) at 0°–5° C. After stirring at 0°–5° C. for 5 min., the reaction was stirred at room temperature for 10 min to complete the reaction. The reaction mixture was re-cooled to 0° C. and thiophene-2-sulfonyl chloride (200 mg, 1.1 mmol) dissolved in dry THF (2 ml) was added dropwise. Stirring was continued for 1 h; during this period the reaction mixture was slowly attained the ambient temperature. THF was removed under reduced pressure. The residue was dissolved in water (10 ml), the pH was adjusted to 10–11 by adding 5N sodium hydroxide solution, and was extracted with ethyl acetate (3×10 ml) to remove the neutral impurities. The aqueous layer was acidified with concentrated HCl (pH 2–3) and extracted with methylene chloride (3×10 ml). The combined organic layers was dried over anhydrous magnesium sulfate and concentrated under reduced pressure to give N-(4-bromo-3-methyl-5-isoxazolyl)thiophene-2-sulfonamide. The pure material was obtained by recrystallization using hexanes/ethyl acetate (110 mg, 34 % yield), m.p. 125°–127° C.

EXAMPLE 2

N-(4-Bromo-3-methyl-5-isoxaxolyl)-5-(3-isoxazolyl)thiophene-2-sulfonamide

A solution of 5-amino-4-bromo-3-methylisoxazole (177 mg, 1.0 mmol) in dry THF (2 ml) was added to a suspension of sodium hydride (60% dispersion in mineral oil, 90 mg, 2.2 mmol) in dry THF (1 ml) at 0°–5° C. After stirring at 0°–5° C. for 5 min, the reaction was warmed to room temperature for 10 min to complete the reaction. The reaction mixture was re-cooled to 0° C., and 5-(3-isoxazolyl)thiophene-2-sulphonyl chloride (273 mg, 1.1 mmol), which had been dissolved in dry THF (2 ml), was added slowly. Stirring was continued for 1 h; during this period the reaction mixture slowly attained ambient temperature. THF was removed under reduced pressure. The residue was dissolved in water (10 ml), the pH was adjusted to 2–3 by adding concentrated HCl, and was extracted with methylene chloride (3×10 ml). The combined organic layers was dried over anhydrous magnesium sulfate and concentrated under reduced pressure to give N-(4-bromo-3-methyl-5-isoxazolyl)-5-(3-isoxazolyl)thiophene-2-sulfonamide. The pure material was obtained by recrystallization using hexanes/ethyl acetate (160 mg, 41% yield), m.p. 120°–123° C.

EXAMPLE 3

N -(4-Bromo-3-methyl-5-isoxaxolyl)-5-(2-pyridyl)thiophene-2-sulfonamide

N-(4-Bromo-3-methyl-5-isoxazolyl)-5-(2-pyridyl)thiophene-2-sulfonamide was prepared in the same manner as described in Example 2 from 5-amino-4-bromo-3-methylisoxazole and 5-(2-pyridyl)thiophene-2-sulphonyl chloride in 40% yield. Purification was achieved by recrystallization from ethyl acetate to give a crystalline solid, m.p. 186°–188° C.

EXAMPLE 4

N-(4-Bromo-3-methyl-5-isoxazolyl)-4,5-dibromothiophene-2-sulfonarnide

N-(4-Bromo-3-methyl-5-isoxazolyl)-4,5-dibromo thiophene-2-sulfonamide was prepared in the same manner as described in Example 2 from 5-amino-4-bromo-3-methylisoxazole and 4,5-dibromothiophene-2-sulphonyl chloride in 45% yield. Purification was achieved by recrystallization from ethyl acetate/hexanes to give a crystalline solid, m.p. 153°–155° C.

EXAMPLE 5

N-(4-Bromo-3-methyl-5-isoxazolyl)-5-chloro-3-methylbenzo[b]thiophene-2-sulfonamide N-(4-Bromo-3-methyl-5-isoxazolyl)-5-chloro-3-methylbenzo[b]thiophene-2-sulfonamide was prepared in the same manner as described in Example 2 from 5-amino-4-bromo-3-methylisoxazole and 5-chloro-3-methylbenzo[b]thiophene-2-sulphonyl chloride in 18% yield. Purification was achieved by recrystallization from ethyl acetate/hexanes to give a crystalline solid, m.p. 153°–155° C.

EXAMPLE 6

N-(4-Bromo-3-methyl-5-isoxazolyl)-5-(4-chlorobenzamidomethyl)thiophene-2-sulfonamide N-(4-Bromo-3-methyl-5-isoxazolyl)-5-(4-chlorobenzamidomethyl)thiophene-2-sulfonamide was prepared in the same manner as described in Example 2 from 5-amino-4-bromo-3-methylisoxazole and 5-(4-chlorobenzamidomethyl)thiophene-2-sulphonyl chloride in 27% yield. The crude product was passed through a silica gel column using hexanes/ethyl acetate as eluent. Purification was effected by recrystallization from ethyl acetate/hexanes to give a crystalline solid, m.p. 210° C. (dec).

EXAMPLE 7

N-(4-Bromo-3-methyl-5-isoxazolyl)-4-benzenesulfonylthiophene-2-sulfonamide

N-(4-Bromo-3-methyl-5-isoxazolyl)-4-benzenesulfonylthiophene-2-sulfonamide was prepared in the same manner as described in Example 2 from 5-amino-4-bromo-3-methylisoxazole and 4-benzenesulfonylthiophene-2-sulphonyl chloride in 26% yield. Purification was achieved by recrystallization from ethyl acetate/hexanes to give a crystalline solid, m.p. 181°–184° C.

EXAMPLE 8

N-(4-Bromo-3-methyl-5-isoxazolyl)-4-bromo-5-chloro-thiophene-2-sulfonamide

N-(4-Bromo-3-methyl-5-isoxazolyl)-4-bromo-5-chlorothiophene-2-sulfonamide was prepared in the same manner as described in Example 2 from 5-amino-4-bromo-3-methylisoxazole and 4-bromo-5-chlorothiophene-2-sulphonyl chloride in 25% yield. Purification was achieved by recrystallization from ethyl acetate/hexanes to give a crystalline solid, m.p. 143°–145° C.

EXAMPLE 9

N-(4-Bromo-3-methyl-5-isoxazolyl)-2,5-dichlorothiophene-3-sulfonamide

N-(4-Bromo-3-methyl-5-isoxazolyl)-2,5-dichlorothiophene-3-sulfonamide was prepared in the same manner as described in Example 2 from 5-amino-4-bromo-3-methylisoxazole and 2,5-dichlorolthiophene-3-sulphonyl chloride in 47% yield. Purification was achieved by recrystallization from ethyl acetate/hexanes to give a crystalline solid, m.p. 135°–138° C.

EXAMPLE 10

N -(4- Bromo-3-methyl-5-isoxazolyl)-2,5-di methylthiophene-3-sulfonamide

N-(4-Bromo-3-methyl-5-isoxazolyl)-2,5-dimethylthiophene-3-sulfonamide was prepared in the same manner as described in Example 1 from 5-amino-4-bromo-3-methylisoxazole and 2,5-dimethylthiophene-3-sulphonyl chloride in 55% yield. Purification was achieved by recrystallization from ethyl acetate/hexanes to give a crystalline solid, m.p. 77°–80° C.

EXAMPLE 11

N-(4-Bromo-3-methyl-5-isoxazolyl)-4,5-dichlorothiophene-2-sulfonamide

N-(4-Bromo-3-methyl-5-isoxazolyl)-4,5-dichlorothiophene-2-sulfonamide was prepared in the same manner as described in Example 1 from 5-amino-4-bromo-3-methylisoxazole and 4,5-dichlorothiophene-2-sulphonyl chloride in 42% yield. Purification was achieved by recrystallization from ethyl acetate/hexanes to give a crystalline solid, m.p. 135°–138° C.

EXAMPLE 12

N-(4-Bromo-3-methyl-5-isoxazolyl)-2,5-dichloro-4-bromothiophene-3-sulfonamide N-(4-Bromo-3-methyl-5-isoxazolyl)-2,5-dichloro-4-bromothiophene-3-sulfonamide was prepared in the same manner as described in Example 1 from 5-amino-4-bromo-3-methylisoxazole and 4-bromo-2,5-dichlorothiophene-3-sulfonyl chloride in 58% yield. Purification was achieved by recrystallization from ethyl acetate/hexanes to give a crystalline solid, m.p. 146°–149° C.

EXAMPLE 13

N-(4-Bromo-3-methyl-5-isoxazolyl)-2-{3-[1-methyl-5-(trifluoromethyl)pyrazolyl]}thiophene-5-sulfonamide N-(4-Bromo-3-methyl-5-isoxazolyl)-2-{3-[1-methyl-5-(trifluoromethyl)pyrazolyl]}thiophene-5-sulfonamide was prepared in the same manner as described in Example 1 from 5-amino-4-bromo-3-methylisoxazole and 2-{3-[1-methyl-5-(trifluoromethyl)pyrazolyl]}thiophene-5-sulphonyl chloride in 30% yield. Purification was achieved by recrystallization from ethyl acetate/hexanes to give a crystalline solid, m.p. 121°–123° C.

EXAMPLE 14

N-(4-Bromo-5-methyl-3-isoxaxolyl) thiophene-2-sulfonamide

Thiophene-2-sulphonyl chloride (183 mg, 1 mmol) was added to a solution of 3-amino-4-bromo-5-methylisoxazole (177 mg, 1 mmol) in dry pyridine (0.5 ml). The reaction mixture was stirred at room temperature for 3 h. Pyridine was removed under reduced pressure and the residue was partitioned between water and ethyl acetate. The organic layer was washed with 1N HCl (3×10 ml), brine (10 ml) and dried over anhydrous magnesium sulfate. Evaporation of the solvents left an oily residue which was solidified at −20° C. and then purified by recrystallization from ethyl acetate/hexanes, to give the pure product (51% yield) as a tan solid, m.p. 156°–158° C.

EXAMPLE 15

N-(4-Bromo-3-methyl-5-isoxazolyl)- 5-benzenesulfonylthiophene-2-sulfonamide

N-(4-Bromo-3-methyl-5-isoxazolyl)-5-benzenesulfonylthiophene-2-sulfonamide was prepared in the same manner as described in Example 2 from 5-amino-4-bromo-3-methylisoxazole and 5-benzenesulfonylthiophene-2-sulphonyl chloride in 59% yield. Purification was achieved by recrystallization from ethyl acetate/hexanes to give a crystalline solid, m.p. 139°–142° C.

EXAMPLE 16

N-(4-Bromo-3-methyl-5-isoxazolyl)- 2-(carbomethoxy)thiophene-3-sulfonamide

N-(4-Bromo-3-methyl-5-isoxazolyl)-2-(carbomethoxy)thiophene-3-sulfonamide was prepared in the same manner as described in Example 2 from 5-amino-4-bromo-3-methylisoxazole and 2-(carbomethoxy)thiophene-3-sulphonyl chloride in 73% yield. Purification was achieved by recrystallization from ethyl acetate/hexanes to give a crystalline solid, m.p. 198°–200° C.

EXAMPLE 17

N-(4-Bromo-3-methyl-5-isoxazolyl)- 2-(carboxyl)thiophene-3-sulfonamide

N-(4-Bromo-3-methyl-5-isoxazolyl)-2-(carbomethoxy)thiophene-3-sulfonamide (EXAMPLE 16) (1.5 g, 3.95 mmol) was dissolved in methanol (10 ml). Sodium hydroxide pellets (1 g, 25 mmol) and few drops of water were then added. The resultant solution was stirred for 16 h at ambient temperature. Methanol was removed under reduced pressure. The residue was diluted with water and was extracted with ethyl acetate (2×10 ml). The aqueous layer was acidified (pH=2) with concentrated hydrochloric acid and was extracted with ethyl acetate (2×60 ml). The combined organic layers was dried over anhydrous magnesium sulfate and filtered. Removal of the solvent gave N-(4-bromo-3-methyl-5-isoxazolyl)-2-(carbomethoxy)thiophene-3-sulfonamide (1.2 g, 82% yield), which was purified by silica gel column chromatography using ethyl acetate as eluent, m.p. 188°–194° C.

EXAMPLE 18

N-(4-Bromo-3-methyl-5-isoxazolyl)- 2-(N-phenylcarboxamide)thiophene-3-sulfonamide Aniline (0.093 g, 1 mmol) and 1-ethyl-3'[3-dimethylaminopropyl]carbodiimide (EDCl) (0.191 g, 1mmol) were added to N-(4-bromo-3-methyl-5-isoxazolyl)-2-(carboxyl)thiophene-3-sulfonamide (0.368 g, 1 mmol) that had been suspended in methylene chloride (5 ml) to produce a clear solution. Stirring was continued for 1 h at ambient temperature. The reaction mixture was diluted with methylene chloride (50 ml) and washed with 3N hydrochloric acid solution (3×50 ml). The combined organic layers was dried over anhydrous magnesium sulfate and filtered. Removal of the solvent under reduced pressure gave N-(4-bromo-3-methyl-5-isoxazolyl)-2-(N-phenylcarboxamide)thiophene-3-sulfonamide. The crude product thus obtained was purified by column chromatography using ethyl acetate as eluent to yield the product (0.32 g, 72% yield, m.p. 168°–170° C.).

EXAMPLE 19

N-(4-Bromo-3-methyl-5-isoxazolyl) 1-(4'-isopropylphenyl)pyrrole-2-sulfonamide and N-(4-Bromo-3-methyl-5-isoxazolyl) 1-(4'-isopropylphenyl)pyrrole-3-sulfonamide A. 1-(4'-isopropylphenyl)pyrrole Glacial acetic acid (100 ml) was added to a mixture of 4-isopropylaniline (10 ml, 72.4 mmol) and 2,5-dimethoxytetrahydrofuran (9.6 ml, 72.4 mmol) and the resulting mixture was refluxed for 1.5 h. The reaction mixture was allowed to cool and acetic acid was removed under reduced pressure. The resulting brown syrup was dissolved in ethyl acetate (200 ml) and washed with water (2×200 ml). The organic layer was dried over magnesium sulfate and filtered. Removal of the solvent gave 1-(4'-isopropylphenyl)pyrrole (13.28 g, 99% yield) as a brown syrup.

B. 1-(4'-isopropylphenyl)pyrrole-2-sulfonic acid

Chlorosulfonic acid (1.82 ml, 27.08 mmol) was slowly added to a solution of 1-(4'-isopropylphenyl)pyrrole (5.01 g, 27.08 mmol) in chloroform (100 ml) at 0° C. The resulting solution was stirred at 0° C. for 1 h and for an additional 1 h at room temperature. Chloroform was removed under reduced pressure. The resultant brown liquid was diluted with ethyl acetate (200 ml) and washed with 1N sodium hydroxide. The aqueous layer was then acidified with concentrated hydrochloric acid (pH<1) and then extracted with chloroform (2×150 ml). The combined organic layers was dried over magnesium sulfate and was filtered. Removal of the solvent gave 1-(4'-isopropylphenyl)pyrrole-2-sulfonic acid as a brown syrup (3 g, 42 % yield).

C. 1-(4'-isopropylphenyl)pyrrole-2-sulfonyl chloride and 1-(4'-isopropylphenyl)pyrrole-3-sulfonyl chloride Phosphorus pentachloride (4.7 g, 22.64 mmol) was slowly added to a solution of 1-(4'-isopropylphenyl)pyrrole-2-sulfonic acid (3 g, 11.32 mmol)in phosphorus oxychloride (8.4 ml, 90.57 mmol). The resulting mixture was heated at 70° C. for 10 h. The reaction mixture was allowed to cool to room temperature, then carefully poured on to crushed ice (500 g) and extracted with chloroform (200 ml). The combined organic layers was dried over anhydrous magnesium sulfate. This was filtered and removal of the solvent yielded a 4:1 mixture of 1-(4'-isopropylphenyl)pyrrole-2-sulfonyl chloride and 1-[4'-isopropylphenyl)pyrrole-3-sulfonyl chloride (2.5 g, 78%) as a brown oil.

D. N-(4-Bromo-3-methyl-5-isoxazolyl) 1-(4'-isopropylphenyl)pyrrole-2-sulfonamide and N-(4-Bromo-3-methyl-5-isoxazolyl) 1-(4'-isopropylphenyl)pyrrole-3-sulfonamide N-(4-Bromo-3-methyl-5-isoxazolyl) 1-(4'-isopropylphenyl)pyrrole-2-sulfonamide and N-(4-bromo-3-methyl-5-isoxazolyl) 1-(4'-isopropylphenyl)pyrrole-3-sulfonamide were prepared in the same manner as described in Example 2 from 5-amino-4-bromo-3-methylisoxazole and a mixture of 1-(4'-isopropylphenyl)pyrrole-2-sulfonyl chloride and 1-(4'-isopropylphenyl)pyrrole-3-sulfonyl chloride in 65% combined yield. The mixture was subjected to preparative HPLC to give N-(4-bromo-3-methyl-5-isoxazolyl) 1-(4'-isopropylphenyl)pyrrole-2-sulfonamide (retention time 22.85 min, 5% to 95% acetonitrile in water with 0.1% TFA over 30 min period, $C_{18}$ analytical column) and N-(4-bromo-3-methyl-5-isoxazolyl) 1-(4'-isopropylphenyl)pyrrole-3-sulfonamide (retention time 24.56 min, 5% to 95% acetonitrile in water with 0.1% TFA over 30 min period, $C_{18}$ analytical column) as oils.

EXAMPLE 20

N-(4-Bromo-3-methyl-5-isoxazolyl)- 5-bromothiophene-2-sulfonamide

N-(4-Bromo-3-methyl-5-isoxazolyl)-5-bromothiophene-2-sulfonamide was prepared in the same manner as described in Example 2 from 5-amino-4-bromo-3-methylisoxazole and 5-bromothiophene-2-sulfonyl chloride in 30% yield. Purification was achieved by recrystallization from ethyl acetate/hexanes to give a crystalline solid, m.p. 240° C. (dec).

EXAMPLE 21

N -(4-Bromo-3-methyl-5-isoxaxolyl)- 2-[N-(4-methoxyphenyl)carboxamide] thiophene-3-sulfonamide 4-Methoxyaniline (0.246 g, 2 mmol), bromo-tris-pyrrolidinophosphonium hexafluorophosphate (PyBrop) (0.466 g, 1 mmol) and N,N'-diisopropylethylamine (0.15 ml) were added to N-(4-bromo-3-methyl-5-isoxazolyl)-2-(carboxyl)thiophene-3-sulfonamide (0.368 g, 1 mmol), which had been suspended in methylene chloride (3 ml), resulting in a clear solution. Stirring was continued for 24 h at ambient temperature. The reaction mixture was diluted with methylene chloride (50 ml) and washed with 3N hydrochloric acid solution (3×50 ml) followed by 5% sodium carbonate solution (2×50 ml). The combined organic layers was dried over anhydrous magnesium sulfate and filtered. Removal of the solvent under reduced pressure gave N-(4-bromo-3-methyl-5-isoxazolyl)-2-[N-(4methoxyphenyl)carboxamide] thiophene-3-sulfonamide. The crude product thus obtained was purified by column chromatography using ethyl acetate as eluent. This was recrystallized from ethyl acetate/hexanes to give a crystalline solid, m.p. 202°–205° C. (0.08 g, 17% yield).

EXAMPLE 22

N-(4-Bromo-3-methyl-5-isoxazolyl)- 2-[N-(3-methoxyphenyl)carboxamide] thiophene-3-sulfonamide N-(4-Bromo-3-methyl-5-isoxazolyl)-2-[N-(3-methoxyphenyl)carboxamide]thiophene-3-sulfonamide was prepared in the same manner as described in Example 21 from N-(4-bromo-3-methyl-5-isoxazolyl)-2-(carboxyl)thiophene-3-sulfonamide and 3-methoxyaniline in 23% yield. The crude product was purified by column chromatography using ethyl acetate as eluent. This was recrystallized from ethyl acetate/hexanes to give a crystalline solid, m.p. 200°–202° C.

EXAMPLE 23

N-(4-Bromo-3-methyl-5-isoxazolyl)- 2-[N-(2-methoxyphenyl)carboxamide] thiophene-3-sulfonamide N-(4-Bromo-3-methyl-5-isoxazolyl)-2-[N-(2-methoxyphenyl)carboxamide]thiophene-3-sulfonamide was prepared in the same manner as described in Example 21 from N-(4-Bromo-3-methyl-5-isoxazolyl)-2-(carboxyl)thiophene-3-sulfonamide and 2-methoxyaniline in 26% yield. The crude product was purified by column chromatography using ethyl acetate as eluent. This was recrystallized from ethyl acetate/hexanes to give a crystalline solid, m.p. 74°–80° C.

EXAMPLE 24

N -(4-Bromo-3-methyl-5-isoxazolyl)- 2-(N-benzylcarboxamide)thiophene- 3-sulfonamide Benzylamine (0.21 4 g, 2 mmol), benzotriazole-1-yl-oxytris(dimethylamino)phosphonium hexafluorophosphate (Bop)(0.442 g, 1 mmol) and N,N'-diisopropylethylamine (0.15 ml) were added to N-(4-bromo-3-methyl-5-isoxazolyl)-2-(carboxyl)thiophene-3-sulfonamide (0.368 g, 1 mmol), which had been suspended in methylene chloride (3 ml). The resultant solution was stirred for 14 h at ambient temperature. This was diluted with methylene chloride (50 ml) and washed with 3N hydrochloric acid (3×50 ml) followed by 5% sodium carbonate solution (2×50 ml). The combined organic layers was dried over anhydrous magnesium sulfate and filtered. Removal of the solvent under reduced pressure gave N-(4-bromo-3-methyl-5-isoxazolyl)-2-(N-benzylcarboxamide)thiophene-3-sulfonamide. The crude product was purified by column chromatography using ethyl acetate as eluent. Recrystallization from ethyl acetate/hexanes gave a crystalline solid, m.p. 186°–190° C. (0.14 g, 30% yield).

EXAMPLE 25

N-(4-Bromo-3-methyl-5-isoxazolyl)- 2-[N-(4-ethylphenyl)carboxamide] thiophene-3-sulfonamide N-(4-Bromo-3-methyl-5-isoxazolyl)-2-[N-(4-ethylphenyl)carboxamide]thiophene-3-sulfonamide was prepared in the same manner as described in Example 24 from N-(4-bromo-3-methyl-5-isoxazolyl)-2-(carboxyl)thiophene-3-sulfonamide and 4-ethylaniline in 31% yield. The crude product was purified by column chromatography using ethyl acetate as eluent. This was recrystallized from ethyl acetate/hexanes to give a crystalline solid, m.p. 187°–190° C.

EXAMPLE 26

N-(4-Bromo-3-methyl-5-isoxazolyl)-2-[N-(4-biphenyl)carboxamide]thiophene-3-sulfonamide N-(4-Bromo-3-methyl-5-isoxazolyl)-2-[N-(4-biphenyl)carboxamide]thiophene-3-sulfonamide compound was prepared in the same manner as described in Example 24 from N-(4-bromo-3-methyl-5-isoxazolyl)-2-(carboxyl)thiophene-3-sulfonamide and 4-phenylaniline in 26% yield. The crude product was purified by column chromatography using ethyl acetate as eluent. This was recrystallized from ethyl acetate/hexanes to give a crystalline solid, m.p. 205°–212° C. (dec).

EXAMPLE 27

N-(3,4-dimethyl-5-isoxazolyl)-2-(carbomethoxy)thiophene-3-sulfonamide

2-Methoxycarbonylthophene-3-sulfonyl chloride (2.50 g, 10.05 mmol) was added to a solution of 5-amino-3,4-dimethylisoxazole (0.98 g, 8.75 mmol) in dry pyridine (5.0 ml). The reaction mixture was stirred at room temperature for 16 h. Pyridine was removed under reduced pressure and the residue was partitioned between water and dichloromethane. The organic layer was washed with 1N HCl (2×50 ml) and dried over anhydrous magnesium sulfate. Evaporation of the solvents left an oily residue, which, after purification by column chromatography over silica gel (1:1 hexanes/ethyl acetate as eluent), yielded 2.20 mg (65%) of a brown solid. Further purification was achieved by recrystallization from ethyl acetate/hexanes, giving the pure product as a white solid, m.p. 113°–116° C.

EXAMPLE 28

N-(3,4-dimethyl-5-isoxazolyl)-2-(carboxyl)thiophene-3-sulfonamide

N-(3,4-dimethyl-5-isoxazolyl)-2-(carboxyl)thiophene-3-sulfonamide was prepared in the same manner as described in Example 17 from N-(3,4-dimethyl-5-isoxazolyl)-2-(carbomethoxy)thiophene-3-sulfonamide by basic hydrolysis in 94% yield. Purification was achieved by recrystallization from ethyl acetate/hexanes to give a crystalline solid, m.p. 202°–203° C.

EXAMPLE 29

N-(3,4-dimethyl-5-isoxazolyl)-2-(N-phenylcarboxamide)thiophene-3-sulfonamide N-(3,4-dimethyl-5-isoxazolyl)-2-(N-phenylcarboxamide)thiophene-3-sulfonamide was prepared in the same manner as described in Example 18 from N-(3,4-dimethyl-5-isoxazolyl)-2-(carboxyl)thiophene-3-sulfonamide in 40% yield. Purification was achieved by recrystallization from ethyl methanol/water to give a crystalline solid, m.p. 176°–178° C.

EXAMPLE 30

N-(4-Bromo-3-methyl-5-isoxazolyl)-5-(2'-thienyl)thiophene-2-sulfonamide

A. 5-Bromo-2,2'-bithiophene

N-bromosuccinimide (NBS, 1.12 g, 6.3 mmol) was added in small portions to a stirred solution of 1.0 g (6.01 mmol) of 2,2'-bithiophene in 10 ml of glacial acetic acid and 10 ml of chloroform. After stirring for 1 h at room temperature, the mixture was poured into ice-water and extracted into chloroform (75 ml). The organic layer was washed with aqueous sodium bicarbonate solution, water, and then dried over magnesium sulfate and evaporated. The residue was subjected to flash chromatography on silica gel using hexane to give 1.3 g (88%) of a light green solid, m.p. 55°–56° C.

B. 5-Chlorosulphonyl-2,2'-bithiophene

A stirred solution of 5-bromo-2,2'-bithiophene (1.5 g, 6.1 mmol) in 10 ml of dry ether was placed under an argon atmosphere, cooled to –78° C. and 4.3 ml of a 1.7M solution of t-butyllithium was added over 20 min. Stirring was continued at this temperature for an additional 20 min. Sulfur dioxide gas was then bubbled in at –78° C. until a yellow precipitate formed. Bubbling of the sulfur dioxide gas was continued for an additional 3 min and was immediately followed by a dropwise addition of N-chlorosuccinimide (NCS, 902 mg, 6.76 mmol) that had been dissolved in THF. The mixture was warmed to room temperature and stirring was continued for an additional 1.5 h. The mixture was then concentrated and the residue dissolved in ether. The organic layer was washed with water, brine solution and dried over magnesium sulfate. Evaporation of solvent left a pale yellow solid, which was recrystallized from hexane to give 700 mg (44%) of a yellow solid, m.p. 63°–64° C.

C. N-(4-Bromo-3-methyl-5-isoxazolyl)-5-(2'-thienyl)thiophene-2-sulfonamide

N-(4-Bromo-3-methyl-5-isoxazolyl)-5-(2'-thienyl)thiophene-2-sulfonamide was prepared in the same manner as described in Example 2. Reaction of 2-chlorosulphonyl-5,2'-bithiophene (300 mg, 1.14 mmol) with 5-amino-4-bromo-3-methylisoxazole (183 mg, 1.03 mmol) yielded, after flash chromatography using 10% MeOH/CHCl$_3$, 430 mg (94%) of a pale brown solid, m.p. 210° C.

EXAMPLE 31

N-(4-Bromo-3-methyl-5-isoxazolyl)thiophene-3-sulfonamide

A. Thiophene-3-sulfonyl chloride

A stirred solution of 3-bromothiophene (1.5 g, 9.2 mmol) in 10 ml of dry ether was placed under an argon atmosphere and cooled to –78° C. Over the course of 20 min, a solution of t-butyllithium (5.6 ml of a 1.7M) was added and stirring was continued at this temperature for an additional 20 min. Sulfur dioxide gas was then bubbled in at –78° C. and the solution was warmed to 0° C., whereupon NCS (1.47 g, 12 mmol) in 8 ml of THF, was added dropwise. After warming to room temperature, stirring was continued for an additional 1 hour, after which, evaporation of solvents left 1.55 g of a brown oil. Flash chromatography over silica gel using hexanes yielded 1.24 g (74%) of a yellow oil which solidified on standing to give a yellow crystalline solid, m.p. 38°–39° C.

B. N-(4-Bromo-3-methyl-5-isoxazolyl)thiophene-3-sulfonamide

N-(4-Bromo-3-methyl-5-isoxazolyl)thiophene-3-sulfonamide was prepared in the same manner as described in Example 2 from thiophene-3-sulfonyl chloride with 5-amino-4-bromo-3-methylisoxazole in 22% yield. Purification by column chromatography using 10% MeOH/CHCl$_3$ as eluent gave a pale brown oil.

EXAMPLE 32

N-(3,4-dimethyl-5-isoxazolyl-5-phenylthiophen-2-sulfonamide

A. N-(3,4-dimethyl-5-isoxazolyl)-5-bromothiophene-2-sulfonamide

A solution of 5-bromothiophene-2-sulfonyl chloride (2.75 g, 10 mmol) and 5-amino-3,4-dimethylisoxazole (1.07 g, 9.57 mmol) in pyridine containing a catalytic amount of 4-dimethylaminopyridine (DMAP, 10 mg) was stirred at room temperature for a period of 3 h. The solution was heated at 50° C. for an additional 1.5 h to drive the reaction to completion as judged by TLC. The pyridine was removed under reduced pressure and the residue, after extraction into ethyl acetate, was washed with 1N HCl (2×25 ml), water (1×25), brine solution, (1×25 ml) and dried over magnesium sulfate. Evaporation of solvent left a viscous brown gum, which was subjected to flash chromatography. Elution with 3% methanol hexanes gave 246 mg (10%) of pure sulfonamide.

B. N.(methoxyethoxymethyl)-N-(3,4-dimethyl-5-isoxazolyl)-5-bromothiophene-2-sulfonamide N-(4-Methyl-3-methyl-5-isoxazolyl)-5-bromothiophene-2-sulfonamide (680 mg, 2 mmol) in dry THF (2 ml) was added to sodium hydride (121 mg of a 60% oil dispersion, 3 mmol) in dry THF (1 ml). The resulting suspension was cooled to 0° C. and methoxy ethoxymethyl chloride (334 mg, 2.68 mmol) was added dropwise via syringe. The solution was warmed to room temperature, and stirring continued overnight. Evaporation of solvent left an oil that was extracted into ethyl acetate, washed with brine, dried over magnesium sulfate and evaporated. Flash chromatography of the residue on silica gel using 10–15% ethylacetate/hexanes yielded 480 mg (56%) of a colorless oil.

C. N-(methoxyethoxymethyl)-N-(3,4-dimethyl-5-isoxazolyl)-5-phenylthiophene-2-sulfonamide Sodium carbonate (2 ml of a 2M aqueous solution) followed by phenyl boronic acid (86 mg, 0.71 mmol) in 2 ml of 95% ethanol were added to a solution of N-(methoxyethoxymethyl)-N-(4-methyl-3-methyl-5-isoxazolyl)-5-bromothiophene-2-sulfonamide (200 mg, 0.47 mmol) and tetrakis (triphenylphosphine) palladium (0) (23 mg, 0.02 mmol) in dry benzene (4 ml) under argon. The mixture was refluxed for 12 h, diluted with 5 ml of water and extracted into ethyl acetate (3×25 ml). The combined organic extracts was washed with brine (1×25 ml), dried and evaporated. The residue was flash chromatographed on silica gel using 25% ethylacetate/hexanes to afford 123 mg (62%) of the sulfonamide as a colorless gum.

D. N-(3,4-dimethyl-5-isoxazolyl-5-phenylthiophen-2-sulfonamide

HCl (3 ml of a 3N aqueous solution) was added to a solution of N-(methoxyethoxymethyl)-N-(3,4-dimethyl-5-isoxazolyl)-5-Phenylthiophene-2-sulfonamide (100 mg, 0.24 mmol) in 3 ml of 95% ethanol and the resulting mixture was refluxed for 6 h. The mixture was then concentrated, diluted with 5 ml of water, neutralized with saturated aqueous sodium bicarbonate solution and acidified to pH 4 using glacial acetic acid. The mixture was extracted with ethyl acetate (2×25 ml) and the combined organic extract was washed with brine (1×5 ml), dried and evaporated. Flash chromatography of the residue on silica gel using 2% MeOH/CHCl$_3$ and further purification by reverse phase HPLC yielded 33.4 mg (42%) of the pure sulfonamide as a white powder, m.p. 176°–178° C.

EXAMPLE 33

N-(4-Bromo-3-methyl-5-isoxazolyl)-5-(4-ethylphenyl)thiophene-2-sulfonamide

A. N-(5-Bromothiophene sulfonyl)-pyrrole

Sodium hydride (60% oil dispersion, 191 m.g., 4.78 mmol) was suspended in dry tetrahydrofurn (2 ml) and the resulting cloudy suspension was cooled to 0° C. in an ice bath. Pyrrole (385 mg, 5.75 mmol) in dry tetrahydrofuran (2 ml) was added dropwise over a period at 10 min. The ice bath was removed and the solution was stir red at room temperature until gas evolution ceased (15 minutes), whereupon 5-bromothiophene-2-sulfonyl chloride (1.0 g, 3.82 mmol) previously dissolved in tetrahydrofuran (4.0 ml) was added dropwise through a steel cannula. After stirring for 1 h at room temperature, the mixture was filtered through Celite. The filter pad rinsed with tetrahydrofuran. The filtrate was evaporated, which left a light brown solid that was recrystallized from methanol to produce the sulfonamide (821 mg, 74% yield) as a white powder.

B. 4-Ethylphenyl boronic acid

A solution of 1-bromo-4-ethyl benzene (2.0 g, 11 mmol) in dry ether (5 ml) was added to magnesium turnings (311 mg, 13 mmol), which had been suspended in dry ether, by a dropwise addition. After addition was complete, the suspension was refluxed for a period of 15 min after which nearly all of the magnesium had reacted. This solution was then added to trimethy borate (1.12 g, 11 mmol) previously dissolved in ether (5 ml) at −78° C., the solution was warmed to room temperature and stirred for 90 min. The reaction was quenched by the addition of 10% aqueous HCl (2 ml) and the solution was extracted with ether. The combined ether extracts was extracted with 1M NaOH (2×20 ml), the aqueous extracts were acidified with dilute HCl to pH 2 and extracted with ether (2×25 ml). The combined ether extracts was washed once with water (10 ml), dried and evaporated to produce a white solid (676 mg, 38% yield), m.p. 138°–140° C.

C. N-(Pyrrole)-5-(4-ethylphenylthiophene)-2-sulfonamide

N-(Pyrrole)-5-(4-ethylphenylthiophene)-2-sulfonamide was prepared, in the same manner as described in Example 32C, from 4-ethylphenylboronic acid and N-(5-bromothiophenesulfonyl)pyrrole. Purification by column chromatography using 10% ethyl acetate/hexanes gave the pure sulfonamide as a tan solid in 81% yield.

D. 5-Chlorosulphonyl-2-(4-ethylphenyl)thiophene

A solution of N-(pyrrole)-5-(4-ethylphenylthiophene)-2-sulfonamide (100 mg, 0.32 mmol) and 6N sodium hydroxide (1 ml) in methanol (1.5 ml) was refluxed for approximately 6 h. Evaporation of solvents and drying in vacuo resulted in an oil. Phosphorus oxychloride (258 ml, 2.52 mmol) and phosphorus pentachloride (131 mg, 0.63 mmol) were added to the oil and the resulting brown suspension was heated at 50° C. for 3 h. The resulting clear brown solution was carefully added to about 20 ml of crushed ice and then extracted with ethyl acetate (3×25 ml). The combined organic layers was washed with brine (2×5 ml), dried (MgSO$_4$) and evaporated to leave an oily residue. Flash chromatography over silica gel using 2% ethyl acetate/hexanes yielded (53 mg, 59%) of the pure sulphonyl chloride as a pale yellow oil.

D. N-(4-Bromo-3-methyl-5-isoxazolyl)-5-(4-ethylphenyl)thiophene-2-sulfonamide

N-(4-Bromo-3-methyl-5-isoxazolyl)-5-(4-ethylphenyl)thiophene-2-sulfonamide was prepared in the same manner as described in Example 2. Reaction of 5-chlorosulphonyl-2-(4-ethylphenyl)thiophene (47.1 mg, 11.16 mmol) with 5-amino-4-bromo-3-methyl isoxazole (29 mg, 0.16 mmol) yielded, after flash chromatography using 10% MeOH/CHCl₃, a pale brown solid (46 mg, 66% yield), m.p. 172°–175° C.

EXAMPLE 34

N-3,4-dimethyl-5-isoxaxolyl)benzo[b]thiophene-2-sulfonamide

A. Benzo[b]thiophene-2-sulfonyl chloride

Benzo[b]thiophene (1.50 g, 11.2 mmol) was stirred at 0° C. in 20 ml of THF. t-Butyllithium (t-BuLi, 1.7M, 16.8 mmol, 9.9 ml) was slowly added over a 5 minute period. Fifteen minutes later, SO₂ was flushed into the reaction flask and a thick white precipitate formed. The reaction mixture was stirred for 15 minutes at 0° C. and then NCS (1.64 g, 12.3 mmol) was added. The reaction was warmed to 25° C. and stirred for 30 min. It was then poured into ethyl acetate (150 ml) and washed with brine (3×100 ml). The organic phase was dried with MgSO₄, filtered and concentrated to collect 2.29 g of a brown oil. The brown oil was subjected to flash chromatography (5% ethyl acetate/hexanes), which provided a yellow tan solid (1.39 g, 53% yield).

B. N-(3,4-dimethyl-5-isoxazolyl)benzo[b]thiophene-2-sulfonamide 3,4-Dimethyl-5-amino-isoxazole (0.224 g, 2.0 mmol) and 50 mg of DMAP were stirred in 5 ml of pyridine at 25° C. The benzo[b]thiophene-2-sulfonyl chloride (0.16 g, 2.6 mmol) was added and the dark brown-yellow reaction mixture was poured into 100 ml of ethyl acetate and washed with 2% HCl (3×50 ml). The organic phase was dried with MgSO₄, filtered and concentrated to collect 0.61 g of a brown oil/solid. The brown oil/solid was subjected to flash chromatography (30% Ethyl acetate/Hexanes) to provide 0.37 g of a light brown solid. This was stirred in 10 ml of methanol and 0.5 g of NaOH. The methanolic solution was heated for reflux for 1 h, then cooled to 25° C. and the methanol was removed in vacuo. The resulting residue was acidified to pH 1 with 2% HCl (100 ml) and extracted with ethyl acetate (2×50 ml) The organic phase was dried with MgSO₄, filtered and concentrated to collect 0.225 g of a yellow-orange solid. This was recrystallized from CHCl₃/Hexanes to produce a light tan-yellow solid (0.194 g, 31% yield), m.p. 157°–160° C.

EXAMPLE 35

N-(3,4-Dimethyl-5-isoxazolyl)benzo[b]furan-2-sulfonamide

A. Benzo[b]furan-2-sulfonyl chloride

Benzo[b]furan-2-sulfonyl chloride was prepared as in Example 34A from benzo[b]furan (1.61 g, 13.6 mmol), t-BuLi (1.7M, 17.7 mmol, 10.4 ml) and NCS (2.0 g, 15.0 mmol). Flash chromatography (5% ethyl acetate/hexanes) yielded a brown solid (1.84 g, 62% yield).

B. N-(3,4-Dimethyl-5-isoxazolyl)benzo[b]furan-2-sulfonarnide

N-(3,4-Dimethyl-5-isoxazolyl)benzo[b]furan-2-sulfonamide was prepared, in the same manner as described in Example 34B, from 3,4-dimethyl-5-amino isoxazole (78 mg, 0.70 mmol) and benzo[b]furan-2-sulfonyl chloride (0.46 g, 2.1 mmol) Flash chromatography (30% ethyl acetate/hexanes) provided 0.186 g of a light yellow solid, which was treated with 31 mg of NaOH in 10 ml of methanol at 25° C. for 30 minutes. Recrystallization from CHCl₃/hexanes yielded a light tan solid (90 mg, 44% yield), m.p. 160.5°–163° C.

EXAMPLE 36

N -(3,4-dimethyl-5-isoxaxolyl)furan-2-sulfonamide

A. Furan-2-sulfonyl chloride

Furan-2-sulfonyl chloride was prepared as in Example 34A from furan (0.96 g, 14.2 mmol), t-BuLi (1.7M, 17 mmol, 10 ml) and NCS (2.27 g, 17 mmol) using ether (30 ml) as the solvent. Flash chromatography (5% ethyl acetate/hexanes) produced a yellow liquid (1.22 g, 52% yield).

B. N-(3,4-dimethyl-5-isoxazolyl)furan-2-sulfonamide

N-(3,4-dimethyl-5-isoxazolyl)furan-2-sulfonamide was prepared as described in Example 34B from 3,4-dimethyl-5-amino isoxazole (0.122 g, 1.0 mmol), furan-2-sulfonyl chloride (0.50 g, 3.0 mmol) and NaOH (64 mg). Flash chromatography (50% ethyl acetate/hexanes) yielded 70 mg of a yellow solid. Recrystallization from CHCl₃/hexanes produced an off-white solid (46 mg, 29% yield), m.p 107°–110° C.

EXAMPLE 37

N-(3,4-Dimethyl-5-isoxazolyl)-3-methoxy-2-thiophene sulfonamide

A. 3-methoxy-2-thiophenesulfonyl chloride

Chlorosulfonic acid (ClSO₃H, 2.31 g, 19.62 mmol) was slowly added at 0° C. to a solution of 3-methoxythiophene (2.29 g, 19.62 mmol) in CHCl₃ (80 ml) The resulting mixture was stirred at 0° C. for 30 min. The solvent was evaporated under reduced pressure, at room temperature, the residue was suspended in POCl₃ (15 ml, 156.96 mmol), and PCl₅ (8.2 g, 39.24 mmol) was added slowly. The reaction was stirred at 60° C. for 18 h, then cooled to room temperature and poured onto crushed ice (200 g). The aqueous mixture was extracted with CHCl₃ (2×150 ml) and the combined organic layers was dried (MgSO₄). The solid was removed by filtration and the filtrate was concentrated to give 3-methoxy-2-thiophenesulfonyl chloride as a brown oil (1.81 g, 43% yield).

B. N-(3,4-dimethyl-5-isoxazolyl)-3-methoxy-2-thiophene sulfonamide

Sodium hydride (1.02 g, 25.56 mmol, 60% dispersion in mineral oil) was slowly added to a solution of 3-methoxy-2-thiophenesulfonyl chloride (1.18 g, 8.52 mmol) and 3,4-dimethyl-5-aminoisoxazole (1.05 g, 9.37 mmol) in THF (20 ml) at room temperature. The resulting mixture was refluxed for 4 h. THF was removed under reduced pressure. The residue was dissolved in water (10 ml), the pH was adjusted to 10–11 by adding 5N sodium hydroxide solution, and was extracted with ethyl acetate (3×10 ml) to remove the neutral impurities. The aqueous layer was acidified with concentrated HCl (pH 2–3) and extracted with methylene chloride (3×10 ml). The combined organic layers was dried over anhydrous magnesium sulfate to produce a crude oil. Further purification by reverse phase HPLC yielded a yellow oil (retention time 14.94 min, 5% to 95% acetonitrile in H₂O with 0.1% TFA over 30 min period, C₁₈ analytical column).

EXAMPLE 38

N-(4-Bromo-3-methyl-5-isoxazolyl)-3-phenyl-2-thiophene sulfonarnide and N-(4-Bromo-3-methyl-5-isoxazolyl)4-phenyl-2-thiophene sulfonamide A. 3-phenyl-2-thiophenesulfonyl chloride and 4-phenyl-2-thiophenesulfonyl chloride Butyllithium (2.38M, 17.2 ml, 41.03 mmol) was slowly added to a solution of 3-phenylthiophene (5.47 g, 34.2 mmol) in Et$_2$O (25 ml) at 0° C. The ice bath was removed, the mixture was stirred at room temperature for 2 h, cooled to –30° C. (CO$_2$/acetone) and SO$_2$ gas was bubbled through the reaction mixture for 20 min. A solution of NCS (6.06 g, 44.5 mmol) in THF (20 ml) was then added. The reaction was allowed to warm to room temperature and stirred for 16 h. The crude mixture was filtered, and the solid was washed with Et$_2$O. The combined organic layers was concentrated and the residue was chromatographed (hexanes/CHCl$_3$) to give 3-phenyl-2-thiophenesulfonyl chloride and 4-phenyl-2-thiophenesulfonyl chloride as a 1:1 mixture (1.46 g, 16.5%, while solid).

B. N-(4-Bromo-3-methyl-5-isoxazolyl)-3-phenyl-2-thiophene sulfonamide and N-(4-Bromo-3-methyl-5-isoxazolyl)-4-phenyl-2-thiophene sulfonamide N-(4-Bromo-3-methyl-5-isoxazolyl)-3-phenyl-2-thiophene sulfonamide and N-(4-bromo-3-methyl-5-isoxazolyl)-4-phenyl-2-thiophene sulfonamide were prepared as described in Example 1. A fraction of the crude mixture of products was purified by HPLC to give N-(4-bromo-3-methyl-5-isoxazolyl)-3-phenyl-2-thiophene sulfonamide (light brown solid, retention time 20.48 min, 5% to 95% acetonitrile in water with 0.1% TFA over 30 min C$_{18}$ analytical column, m.p. 105°–107° C.) and N-(4-bromo-3-methyl-5-isoxazolyl)-4-phenyl-2-thiophene sulfonamide (dull yellow solid, m.p. 108°–110° C., retention time 21.35 min, same conditions).

EXAMPLE 39

Other sulfonamides of interest herein that can be prepared by methods analogous to those set forth in Examples 1–38 include the following compounds: N-(4-chloro-3-methyl-5-isoxazolyl)-2-(phenylaminocarbonyl)thiophene-3-sulfonamide; N-(4-chloro-3-methyl-5-isoxazolyl)-5-benzylthiophene-2-sulfonamide; N-(4-chloro-3-methyl-5-isoxazolyl)-3-benzylthiophene-2-sulfonamide; N-(4-chloro-3-methyl-5-isoxazolyl)-3-phenethylthiophene-2-sulfonamide; N-(4-bromo-3-methyl-5-isoxazolyl)-styrylthiophene-2-sulfonamide; N-(4-bromo-3-methyl-5-isoxazolyl)-2-styrylthiophene-3-sulfonamide; N-(4-bromo-3-methyl-5-isoxazolyl)-2-phenoxythiophene-3-sulfonamide; N-(4-bromo-3-methyl-5-isoxazolyl)-2-benzenesulfonylthiophene-3-sulfonamide; N-(4-bromo-3-methyl-5-isoxazolyl)-2-phenylthiophene-3-sulfonamide; N-(4-bromo-3-methyl-5-isoxazolyl)-2-aminothiophene-3-sulfonamide; N-(4-bromo-3-methyl-5-isoxazolyl)-2-(benzoylamino)thiophene-3-sulfonamide; N-(4-bromo-3-methyl-5-isoxazolyl)-3-benzylthiophene-2-sulfonamide; N-(4-bromo-3-methyl-5-isoxazolyl)-3-phenethylthiophene-2-sulfonamide; N-(4-bromo-3-methyl-5-isoxazolyl)-5-benzylthiophene-2-sulfonamide; N-(4-bromo-3-methyl-5-isoxazolyl)-2-[(N-phenyl)methylaminocarbonyl]thiophene-3-sulfonamide; N-(4-bromo-3-methyl-5-isoxazolyl)-5-benzylfuran-2-sulfonamide; N-(4-bromo-3-methyl-5-isoxazolyl)-5-(phenylthio)furan-2-sulfonamide; N-(4-bromo-3-methyl-5-isoxazolyl)-5-(hydroxymethyl)furan-2-sulfonamide; N-(4-bromo-3-methyl-5-isoxazolyl)-5-(carbomethoxy)furan-2-sulfonamide; N-(4-bromo-3-methyl-5-isoxazolyl)-2,5-dimethylfuran-3-sulfonamide; N-(4-bromo-3-methyl-5-isoxazolyl)-5-(4-isopropylphenyl)thiophene-2-sulfonamide; N-(4-bromo-3-methyl-5-isoxazolyl)-5-(4-propylphenyl)thiophene-2-sulfonamide; N-(4-bromo-3-methyl-5-isoxazolyl)-3-(phenylaminocarbonyl)thiophene-2-sulfonamide; N-(4-bromo-3-methyl-5-isoxazolyl)-2-benzylthiophene-3-sulfonamide; N-(4-bromo-3-methyl-5-isoxazolyl)-2-phenylthiophene-3-sulfonamide; N-(4-bromo-3-methyl-5-isoxazolyl)-2-(dimethylaminocarbonyl)thiophene-3-sulfonamide; N-(4-bromo-3-methyl-5-isoxazolyl)-2-(di-iso-propylaminocarbonyl)thiophene-3-sulfonamide; N-(4-bromo-3-methyl-5-isoxazolyl)-2-(diethylaminocarbonyl)thiophene-3-sulfonamide; N-(4-bromo-3-methyl-5-isoxazolyl)-5-(4-iso-butylphenyl)furan-2-sulfonamide; N-(4-bromo-3-methyl-5-isoxazolyl)-5-styrylfuran-2-sulfonamide; and N-(4-bromo-3-methyl-5-isoxazolyl)-5-styrylthiophene-2-sulfonamide.

EXAMPLE 40

Assays for identifying compounds that exhibit endothelin antagonistic and/or agonist activity Compounds that are potential endothelin antagonists are identified by testing their ability to compete with $^{125}$I-labeled ET-1 for binding to human ET$_A$ receptors or ET$_B$ receptors present on isolated cell membranes. The effectiveness of the test compound as an antagonist or agonist of the biological tissue response of endothelin can also be assessed by measuring the effect on endothelin induced contraction of isolated rat thoracic aortic rings. The ability of the compounds to act as antagonists or agonists for ET$_B$ receptors can be assess by testing the ability of the compounds are to inhibit endothelin-1 induced prostacyclin release from cultured bovine aortic endothelial cells.

A. Endothelin binding inhibition—Binding Test #1: Inhibition of binding to ET$_A$ receptors TE 671 cells (ATCC Accession No. HTB 139) express ET$_A$ receptors. These cells were grown to confluence in T-175 flasks. Cells from multiple flasks were collected by scraping, pooled and centrifuged for 10 min at 190×g. The cells were resuspended in phosphate buffered saline (PBS) containing 10 mM EDTA using a Tenbroeck homogenizer. The suspension was centrifuged at 4° C. at 57,800×g for 15 min, the pellet was resuspended in 5 ml of buffer A (5 mM HEPES buffer, pH 7.4 containing aprotinin (100 KIU/ml)) and then frozen and thawed once. 5 ml of Buffer B (5 mM HEPES Buffer, pH 7.4 containing 10 mM MnCl$_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml and stored at –70° C. until use.

The membrane suspension was diluted with binding buffer (30 mM HEPES buffer, pH 7.4 containing 150 mM NaCl, 5 mM MgCl$_2$, 0.5% Bacitracin) to a concentration of 8 µg/50 µl. $^{125}$I-endothelin-1 (3,000 cpm, 50 mL) was added to 50 pL of either: (A) endothelin-1 (for non specific binding) to give a final concentration 80 nM); (B) binding buffer (for total binding); or (C) a test compound (final concentration 1 nM to 100 µM). The membrane suspension (50 µL), containing up to 8 µg of membrane protein, was added to each of (A), (B), or (C). Mixtures were shaken, and incubated at 4° C. for 16–18 hours, and then centrifuged at 4° C. for 25 min at 2,500×g. The supernatant, containing unbound radioactivity, was decanted and the pellet counted on a Genesys multiwell gamma counter. The degree of inhibition of binding (D) was calculated according to the following equation:

$$\%D = 100 - \frac{(C)-(A)}{(B)-(A)} \times 100$$

Each test was generally performed in triplicate.

B. Endothelin binding inhibition—Binding Test #2: Inhibition of binding to $ET_B$ receptors COS7 cells were transfected with DNA encoding the $ET_B$ receptor, The resulting cells, which express the human $ET_B$ receptor, were grown to confluence in T-150 flasks. Membrane was prepared as described above. The binding assay was performed as described above using the membrane preparation diluted with binding buffer to a concentration of 1 µg/50 µl.

Briefly, the COS7 cells, described above, that had been transfected with DNA encoding the $ET_B$ receptor and express the human $ET_B$ receptor on their surfaces were grown to confluence in T-175 flasks. Cells from multiple flasks were collected by scraping, pooled and centrifuged for 10 rain at 190×g. The cells were resuspended in phosphate buffered saline (PBS) containing 10 mM EDTA using a Tenbroeck homogenizer. The suspension was centrifuged at 4° C. t 57,800×g for 15 min, the pellet was resuspended in 5 ml of buffer A (5 mM HEPES buffer, pH 7.4 containing aprotinin (100 KIU/ml)) and then frozen and thawed once. Five ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml.

The binding assay was performed as described above using the membrane preparation diluted to give 1 µg/50 µl of binding buffer.

C. Test for activity against endothelin-induced contraction of isolated rat thoracic aortic rings The effectiveness of the test compound as an antagonist or agonist of the biological tissue response of endothelin also is assessed by measuring the effect on endothelin induced contraction of isolated rat thoracic aortic rings (see, e.g., Borges et al. (1989) *Eur. J. Pharmacol.* 165:223–230) or by measuring the ability to contract the tissue when added alone.

Compounds to be tested are prepared as 100 µM stocks. If necessary to effect dissolution, the compounds are first dissolved in a minimum amount of DMSO and diluted with 150 mM NaCl. Because DMSO can cause relaxation of the aortic ring, control solutions containing varying concentrations of DMSO were tested.

The thoracic portion of the adult rat aorta is excised, the endothelium abraded by gentle rubbing and then cut into 3 mm ring segments. Segments are suspended under a 2 g preload in a 10 ml organ bath filled with Krebs'—Henseleit solution saturated with a gas mixture of 95% $O_2$ and 5% $CO_2$ (118 mM NaCl, 4,7 mM KCl, 1.2 mM $MgSO_4$, 1.2 mM $KH_2PO_4$, 25 mM $NaHCO_3$, 2.5 mM $CaCl_2$, 10 mM D-glucose) gassed with 95% $O_2$/5% $CO_2$. Changes in tension are measured isometrically and recorded using a Grass Polygraph coupled to a force transducer.

Endothelin is added to the organ bath in a cumulatively increasing manner, and the effects of the test compounds on the concentration-response curve for endothelin-1 are examined. Compounds are added 15 min prior to the addition of endothelin-1.

D. Assay for identifying compounds that have agonist and/or antagonistic activity against $ET_B$ receptors 1. Stimulation of prostacyclin release Since endothelin-1 stimulates the release of prostacyclin from cultured bovine aortic endothelial cells, the compounds that have agonist or antagonist activity are identified by their ability to inhibit endothelin-1 induced prostacyclin release from such endothelial cells by measuring 6-keto $PGF_{1\alpha}$ substantially as described by (Filep et al. (1991). *Biochem. Biophys. Res. Commun.* 177 171–176. Bovine aortic cells are obtained from collagenase-treated bovine aorta, seeded into culture plates, grown in Medium 199 supplemented with heat inactivated 15% fetal calf serum, and L-glutamine (2 mM), penicillin, streptomycin and fungizone, and subcultured at least four times. The cells are then seeded in six-well plates in the same medium. Eight hours before the assay, after the cells reach confluence, the medium is replaced. The cells are then incubated with a) medium alone, b) medium containing endothelin-1 (10 nM), c) test compound alone, and d) test compound+endothelin-1 (10 nM).

After a 15 min incubation, the medium is removed from each well and the concentrations of 6-keto $PGF_{1\alpha}$ are measured by a direct immunoassay. Prostacyclin production is calculated as the difference between the amount of 6-keto $PGF_{1\alpha}$ released by the cells challenged with the endothelin-1 minus the amount released by identically treated unchallenged cells. Compounds that stimulate 6-keto $PGF_{1\alpha}$ release possess agonist activity and those which inhibit endothelin-1 6-keto $PGF_{1\alpha}$ release possess antagonist activity.

2. Inhibition of sarafotoxin 6c induced contraction

Sarafotoxin 6c is a specific $ET_B$ antagonist that contracts rat fundal stomach strips. The effectiveness of tests compounds to inhibit this sarafotoxin 6c-induced contraction of rat fundal stomach strips is used as a measure $ET_B$ antagonist activity. Two isolated rat fundal stomach strips are suspended under a 1 g load in a 10 ml organ bath filled with Krebs'-Henseleit solution containing 10 µM cyclo(D-Asp-Pro-D-VaI-Leu-D-Trp) (BQ-123; see, U.S. Pat. No. 5,114,918 to Ishikawa et al.), 5 µM indomethacin, and saturated with a gas mixture of 95% 02/5% $CO_2$. Changes in tension are measured isometrically and recorded using a Grass Polygraph coupled to a force transducer. Sarafotoxin 6c is added cumulatively to one strip while the second strip is preincubated for 15 rain with a test compound prior to addition of cumulative doses of sarafotoxin 6c. The effects of the test compounds on the concentration-response curve for sarafotoxin 6c are examined.

E. Results

The $IC_{50}$ for each of the compounds of the preceding Examples for $ET_A$ and $ET_B$ receptors has been measured. Almost all of the compounds have an $IC_{50}$ of less than 10 µM for either or both of the $ET_A$ and $ET_B$ receptors. Many of the compounds have an $IC_{50}$ less than about 10 µM, others have an $IC_{50}$ less than about 1 µM and some of the compounds have an $IC_{50}$ less than about 0.1 µM. A number of the compounds have an $IC_{50}$ for $ET_A$ receptors that is substantially less (10 to 100-fold or more) than for $ET_B$ receptors, and, thus are selective for $ET_A$ receptors. Others of the compounds are $ET_B$ selective.

Since modifications will be apparent to those of skill in this art, it is intended that this invention be limited only by the scope of the appended claims.

We claim:

1. A sulfonamide compound of formula (I)

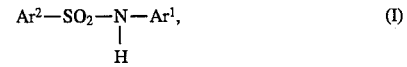

wherein:

43

Ar¹ is selected from the group consisting of isoxazole and isoxazoline groups; and Ar² is a substituted or unsubstituted group selected from thiophenyl, furyl and pyrrolyl.

2. A sulfonamide of claim 1, wherein Ar¹ is selected from the group consisting of the following groups:

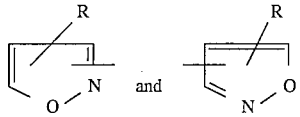

that are unsubstituted or substituted with one or more substituents R, which are each independently selected from the group consisting of H, $NH_2$, halide, pseudohalide, alkyl, alkylcarbonyl, formyl, an aromatic or heteroaromatic group, alkoxyalkyl, alkylamino, alkylthio, arylcarbonyl, aryloxy, arylamino, arylthio, haloalkyl, haloaryl, carbonyl, in which the aryl and alkyl portions, are unsubstituted or substituted, the alkyl portions are straight or branched chains of from about 1 up to about 10–12 carbons, and the aryl portions are substituted or unsubstituted and contain from 3 to about 14 carbon atoms.

3. A sulfonamide of claim 1, wherein Ar¹ is an isoxazolyl group.

4. A sulfonamide of claim 3, that has the formula (II):

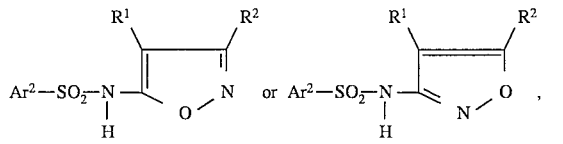

wherein $R^1$ and $R^2$ are selected from (i), (ii) or (iii):
(i) $R^1$ and $R^2$ are each independently selected from the group consisting of H, $NH_2$, $NO_2$, halide, pseudohalide, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons; or,
(ii) $R^1$ and $R^2$ together form $-(CH_2)_n$, where n is 3 to 6; or,
(iii) $R^1$ and $R^2$ together form 1,3-butadienyl.

5. A sulfonamide of claim 4, wherein Ar² is thiophenyl.

6. A sulfonamide of claim 4, wherein Ar² is furyl.

7. A sulfonamide of claim 4, wherein Ar² is pyrrolyl.

8. A sulfonamide of claim 4, wherein $R^1$ is H, lower alkyl, halide or pseudohalide; and $R^2$ is lower alkyl, lower alkenyl, lower alkynl, lower haloalkyl, halide, pseudohalide or hydrogen.

9. A sulfonamide of claim 5, wherein $R^1$ is H, lower alkyl, halide or pseudohalide; and $R^2$ is lower alkyl, lower alkenyl, lower alkynl, lower haloalkyl, halide, pseudohalide or hydrogen.

44

10. A sulfonamide of claim 4 that has formulae (III):

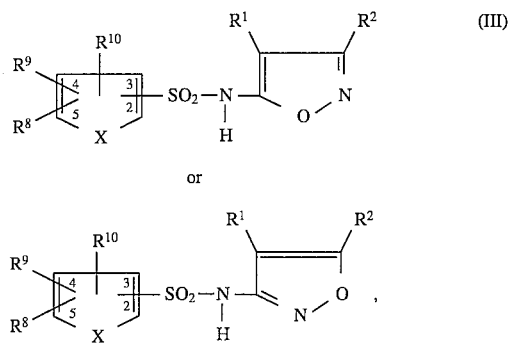

wherein:
X is O, S, NH or $NR^{11}$ in which $R^{11}$, which is hydrogen or contains up to about 30 carbon atoms, is selected from the group consisting of hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0–2; and $R^{15}$, which is selected independently from $R^{11}$, is selected from the group consisting of hydrogen, alkyl, alkenyl, alkynyl, aryl, alkylaryl, heterocycle, aralkyl, aralkoxy, cycloalkyl, cycloalkenyl, cycloalkynyl;
and $R^8$, $R^9$ and $R^{10}$ are selected from (i) or (ii):
(i) $R^8$, $R^9$ and $R^{10}$, which each contain hydrogen or up to about 50 carbon atoms, are each independently selected from the group consisting of hydrogen, halide pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{18}$, $CO_2R^{18}$, SH, $S(O)_nR^{18}$ in which n is 0–2, HNOH, $NR^{18}R^{19}$, $NO_2$, $N_3$, $OR^{18}$, $R^{19}NCOR^{18}$ and $CONR^{19}R^{18}$, in which $R^{19}$ is selected from the group consisting of hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, $C(O)R^{20}$ and $S(O)_nR^{20}$ in which n is 0–2; and $R^{18}$ and $R^{20}$ are each independently selected from the group consisting of hydrogen, alkyl, alkenyl, alkynyl, aryl, alkylaryl, heterocycle, alkoxy, aryloxy, aralkyl, aralkoxy, cycloalkyl, cycloalkenyl or cycloalkynyl; or
(ii) any two of $R^8$, $R^9$ and $R^{10}$ form an aromatic or heteroaromatic ring or an alicyclic or heterocyclic ring, which is saturated or unsaturated, containing from about 3 to about 16 members, and the other of $R^8$, $R^9$ and $R^{10}$ is selected as in (i).

11. The sulfonamides of claim 10, in which at least one of $R^8$, $R^9$, and $R^{10}$ is further substituted with one or more substituents selected from Z, which is selected from the group consisting of hydrogen, halide, pseudohalide, alkyl, alkoxy, alkenyl, alkynyl, aryl, heterocycle, aralkyl, aralkoxy, cycloalkyl cycloalkenyl, cycloalkynyl OH, CN, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$;

$R^{16}$ is selected from the group consisting of hydrogen, alkyl, alkenyl, alkynyl, aryl, alkylaryl, heterocycle, aralkyl, aralkoxy, cycloalkyl, cycloalkenyl and cycloalkynyl;

$R^{12}$ is selected from the group consisting of hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; and $R^{17}$ is selected from the group consisting of hydrogen, alkyl, alkenyl, alkynyl, aryl, alkylaryl, heterocycle, aralkyl, aralkoxy, cycloalkyl, cycloalkenyl or cycloalkynyl.

12. The sulfonamides of claim 10, wherein X is S.
13. The sulfonamides of claim 10, wherein X is O.
14. The sulfonamides of claim 10, wherein X is N.
15. The sulfonamides of claim 14, wherein $R^{11}$ is aryl.
16. A sulfonamide of claim 11, wherein at least two of $R^8$, $R^9$ and $R^{10}$ are hydrogen, halogen or lower alkyl, and the other is selected from the group consisting of hydrogen, halide pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, C(O)$R^{18}$, CO$_2R^{18}$, SH, S(O)$_nR^{18}$ in which n is 0–2, HNOH, NR$^{18}R^{19}$, NO$_2$, N$_3$, OR$^{18}$, $R^{19}$NCOR$^{18}$ and CONR$^{19}R^{18}$.
17. A sulfonamide of claim 16, wherein $R^{19}$ is hydrogen or lower alkyl; and $R^{18}$ is lower aryl.
18. A sulfonamide of claim 17, wherein $R^{18}$ is phenyl.
19. A sulfonamide of claim 18, wherein at least two of $R^8$, $R^9$ and $R^{10}$ are hydrogen, halogen or lower alkyl, and the other is C(O)$R^{18}$, CO$_2R^{18}$,, NR$^{18}R^{19}$, $R^{19}$NCOR$^{18}$ CONR$^{19}R^{18}$.
20. A sulfonamide of claim 18, wherein $R^1$ is Br or Cl or lower alkyl and $R^2$ is lower alkyl, lower haloalkyl, or hydrogen.
21. A sulfonamide of claim 12, wherein at least two of $R^8$, $R^9$ and $R^{10}$ are hydrogen, halogen or lower alkyl, and the other is selected from the group consisting of hydrogen, halide pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, C(O)$R^{18}$, CO$_2R^{18}$, SH, S(O)$_nR^{18}$ in which n is 0–2, HNOH, NR$^{18}R^{19}$, NO$_2$, N$_3$, OR$^{18}$, $R^{19}$NCOR$^{18}$ and CONR$^{19}R^{18}$.
22. A sulfonamide of claim 21, wherein $R^{19}$ is hydrogen, or lower alkyl; and $R^{18}$ is lower aryl.
23. A sulfonamide of claim 22, wherein at least two of $R^8 R^9$ and $R^{10}$ hydrogen, halogen or lower alkyl, and the other is selected from the group consisting of C(O)$R^{18}$, CO$_2R^{18}$, NR$^{18}R^{19}$, $R^{19}$NCOR$^{18}$ and CONR$^{19}R^{18}$.
24. A sulfonamide of claim 23, wherein $R^1$ is Br or Cl or lower alkyl and $R^2$ is lower alkyl, lower haloalkyl, or hydrogen.
25. A sulfonamide of claim 15, wherein at least two of $R^8$, $R^9$ and $R^{10}$ are hydrogen, halogen or lower alkyl, and the other is selected from the group consisting of hydrogen, halide pseudohalide, alkyl, alkoxy, alkenyl, alkynyl, aryl, aryloxy, heterocycle, aralkyl, aralkoxy, cycloalkyl, cycloalkenyl, cycloalkynyl, OH CN, C(O)$R^{18}$, CO$_2R^{18}$, SH S(O)$_nR^{18}$ in which n is 0–2, HNOH, NR$^{18}R^{19}$, NO$_2$, N$_3$, OR$^{18}$, $R^{19}$NCOR$^{18}$ and CONR$^{19}R^{18}$.
26. A sulfonamide of claim 25, wherein $R^{19}$ is hydrogen or lower alkyl; and $R^{18}$ is lower aryl.
27. A sulfonamide of claim 26, wherein $R^{19}$ is hydrogen or lower alkyl; and $R^{18}$ phenyl.
28. A sulfonamide of claim 27, wherein at least two of $R^8$, $R^9$ and $R^{10}$ hydrogen, halogen or lower alkyl, and the other is selected from the group consisting of C(O)$R^{18}$, CO$_2R^{18}$,, NR$^{18}R^{19}$, $R^{19}$NCOR$^{18}$ and CONR$^{19}R^{18}$.
29. A sulfonamide of claim 28, wherein $R^1$ is Br or Cl or lower alkyl and $R^2$ is lower alkyl, lower haloalkyl, or hydrogen.
30. The sulfonamides of claim 16 that are thiophene-2-sulfonamides or thiophene-3-sulfonamides.
31. A sulfonamide of claim 4 that is $ET_A$ selective.
32. A sulfonamide of claim 4 that is $ET_B$ selective.
33. A sulfonamide of claim 6, wherein $R^1$ is H, lower alkyl, halide or pseudohalide; and $R^2$ is lower alkyl, lower alkenyl, lower alkynyl, lower haloalkyl, halide, pseudohalide or hydrogen.

34. A sulfonamide of claim 7, wherein $R^1$ is H, lower alkyl, halide or pseudohalide; and $R^2$ is lower alkyl, lower alkenyl, lower alkynyl, lower haloalkyl, halide, pseudohalide or hydrogen.

35. A sulfonamide of claim 8 that has formulae (III):

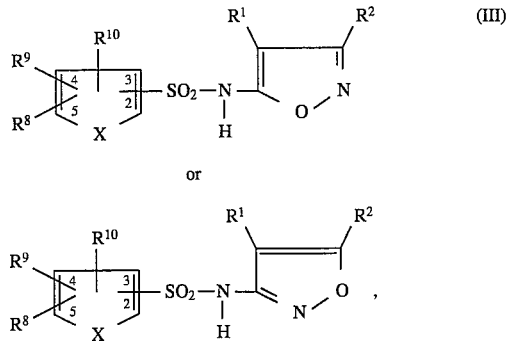

wherein:
X is S; and $R^8$, $R^9$ and $R^{10}$ are selected from (i) or (ii):
(i) $R^8$, $R^9$ and $R^{10}$, which each contain hydrogen or up to about 50 carbon atoms, are each independently selected from the group consisting of hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, C(O)$R^{18}$, CO$_2R^{18}$, SH S(O)$_nR^{18}$ in which n is 0–2, HNOH, NR$^{18}R^{19}$, NO$_2$, N$_3$, OR$^{18}$, $R^{19}$NCOR$^{18}$ and CONR$^{19}R^{18}$, in which $R^{19}$ is selected from the group consisting of hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, C(O)$R^{20}$ and S(O)$_nR^{20}$ in which n is 0–2; and $R^{18}$ and $R^{20}$ are each independently selected from the group consisting of hydrogen, alkyl, alkenyl, alkynyl, aryl, alkylaryl, heterocycle, alkoxy, aryloxy, aralkyl,, aralkoxy, cycloalkyl, cycloalkenyl or cycloalkynyl; or
(ii) any two of $R^8$, $R^9$ and $R^{10}$ form an aromatic or heteroaromatic ring or an alicyclic or heterocyclic ring, which is saturated or unsaturated, containing from about 3 to about 16 members, and the other of $R^8$, $R^9$ and $R^{10}$ is selected as in (i).

36. A sulfonamide of claim 1, wherein all of the alkyl, alkenyl, alkynyl substituents contain from 1 to 12 carbons; and the aryl and heterocyclic substituents, other than Ar$^2$, contain from 3 to 6 carbons in the ring.

37. A compound selected from the group consisting of N-(4-bromo-3-methyl-5-isoxazolyl)-2-(N-phenylcarboxamide)thiophene-3-sulfonamide; N-(3,4-dimethyl-5-isoxazolyl)-2-(N-phenylcarboxamide)thiophene-3-sulfonamide, N-(4-bromo-3-methyl-5-isoxazolyl)-2,5-dimethylthiophene-3-sulfonamide; N-(4-bromo-3-methyl-5-isoxazolyl)-2-(carbomethoxy)thiophene-3-sulfonamide, N-(4-bromo-3-methyl-5-isoxazolyl)thiophene-2-sulfonamide, N-(4-bromo-3-methyl-5-isoxazolyl)-2-[N-(4-biphenyl)carboxamide]thiophene-3-sulfonamide, N-(4-bromo-3-methyl-5-isoxazolyl)-2-[N-(4-ethylphenyl)carboxamide]thiophene-3-sulfonamide, N-(4-bromo-3-methyl-5-isoxazolyl)-2-[N-(benzylcarboxamide]thiophene-3-sulfonamide, N-(4-bromo-3-methyl-5-isoxazolyl)-2-[N-(2-methoxyphenyl)carboxamide]thiophene-3-sulfonamide, N-(4-bromo-3-methyl-5-isoxazolyl)-2-[N-(3-methoxyphenyl)carboxamide]thiophene-3-sulfonamide and N-(4- bromo-3-methyl-5-isoxazolyl)-2-[N-(4-methoxyphenyl)carboxamide]thiophene-3-sulfonamide.

38. A compound selected from the group consisting of N-(4-bromo-3-methyl-5-isoxazolyl)-5-benzenesulfonylthiophene-2-sulfonamide, N-(4-bromo-3-methyl-5-isoxazolyl)-1-(4'-isopropylphenyl)pyrrole-2-sulfonamide, N-(4-bromo-3-methyl-5-isoxazolyl)-1-(4'-isopropylphenyl)pyrrole-3-sulfonamide, N-(4-bromo-3-methyl-5-isoxazolyl)-2-{3-[1-methyl-5-(trifluoromethyl)pyrazolyl]}thiophene-5-sulfonamide, N-(4-bromo-3-methyl-5-isoxazolyl)-2-[N-(4-biphenyl)carboxamide]thiophene-3-sulfonamide, N-(4-bromo-3-methyl-5-isoxazolyl)-2-[N-(4-ethylphenyl)carboxamide]thiophene-3-sulfonamide, N-(4-bromo-3-methyl-5-isoxazolyl)-5-thienylthiophene-2-sulfonamide, and N-(4-bromo-3-methyl-5-isoxazolyl)-5-(4-ethylphenyl)thiophene-2-sulfonamide.

39. The sulfonamide of claim 1 that is N-(4-bromo-3-methyl-5-isoxazolyl)-5-(4-ethylphenyl)thiophene-2-sulfonamide.

40. The sulfonamide of claim 1 that is N-(4-bromo-3-methyl-5-isoxazolyl)-2-(N-phenylcarboxamide)thiophene-3-sulfonamide.

41. The sulfonamide of claim 1 that is N-(4-bromo-3-methyl-5-isoxazolyl)-2,5-dimethylthiophene-3-sulfonamide.

42. The sulfonamide of claim 1 that is N-(4-bromo-3-methyl-5-isoxazolyl)-2-(carbomethoxy)thiophene-3-sulfonamide.

43. The sulfonamide of claim 1 that is N-(4-bromo-3-methyl-5-isoxazolyl)-5-benzenesulfonylthiophene-2-sulfonamide.

44. The sulfonamide of claim 1 that is N-(4-bromo-3-methyl-5-isoxazolyl) 1-(4'-isopropylphenyl)pyrrole-2-sulfonamide.

45. The sulfonamide of claim 1 that is N-(4-bromo-3-methyl-5-isoxazolyl) 1-(4'-isopropylphenyl)pyrrole-3-sulfonamide.

46. The sulfonamide of claim 1 that is N-(4-bromo-3-methyl-5-isoxazolyl)-5-{3-[1-methyl-5-(trifluoromethyl)pyrazolyl]}thiophene-2sulfonamide.

47. The sulfonamide of claim 1 that is N-(4-bromo-5-methyl-3-isoxazolyl)thiophene-2-sulfonamide.

48. The sulfonamide of claim 1 that is N-(4-bromo-3-methyl-5-isoxazolyl)thiophene-2-sulfonamide.

49. The sulfonamide of claim 1 that is N-(4-bromo-3-methyl-5-isoxazolyl)-5-chloro-3-methylbenzo[b]thiophene-2-sulfonamide.

50. The sulfonamide of claim 1 that is N-(3,4-dimethyl-5-isoxazolyl)benzo[b]thiophene-2-sulfonamide.

51. The sulfonamide of claim 1 that is N-(3,4-dimethyl-5-isoxazolyl)benzo[b]furan-2-sulfonamide.

52. The sulfonamide of claim 1 that is N-(3,4-dimethyl-5-isoxazolyl)benzo[b]thiophene-2-sulfonamide.

53. The sulfonamide of claim 1 that is N-(3,4-dimethyl-5-isoxazolyl)furan-2-sulfonamide.

54. The sulfonamide of claim 1 that is N-(3,4-dimethyl-5-isoxazolyl)-3-methoxy-2-thiophene sulfonamide.

55. The sulfonamide of claim 1 that is N-(4-bromo-3-methyl-5-isoxazolyl)-3-phenyl-2-thiophene sulfonamide.

56. The sulfonamide of claim 1 that is N-(4-bromo-3-methyl-5-isoxazolyl)4-phenyl-2-thiophene sulfonamide.

57. A pharmaceutical composition, comprising a compound of claim 1 or a pharmaceutically acceptable salt of a compound of claim 1 in a pharmaceutically acceptable carrier.

58. A pharmaceutical composition, comprising a compound of claim 3 or a pharmaceutically acceptable salt of a compound of claim 3 in a pharmaceutically acceptable carrier.

59. A pharmaceutical composition, comprising a compound of claim 37 or a pharmaceutically acceptable salt of a compound of claim 37 in a pharmaceutically acceptable carrier.

60. A pharmaceutical composition, comprising a compound of claim 38 or a pharmaceutically acceptable salt of a compound of claim 38 in a pharmaceutically acceptable carrier.

61. A method for the treatment of endothelin-mediated diseases, comprising administering an effective amount of one or more compounds of claim 1 or pharmaceutically acceptable salts of the compounds of claim 1, wherein the effective amount is sufficient to ameliorate one or more of the symptoms of the disease.

62. A method for the treatment of endothelin-mediated diseases, comprising administering an effective amount of one or more compounds of claim 3 or pharmaceutically acceptable salts of the compounds of claim 3, wherein the effective amount is sufficient to ameliorate one or more of the symptoms of the disease.

63. A method for the treatment of endothelin-mediated diseases, comprising administering an effective amount of one or more compounds of claim 37 or pharmaceutically acceptable salts of the compounds of claim 37, wherein the effective amount is sufficient to ameliorate one or more of the symptoms of the disease.

64. A method for the treatment of endothelin-mediated diseases, comprising administering an effective amount of one or more compounds of claim 38 or pharmaceutically acceptable salts of the compounds of claim 38, wherein the effective amount is sufficient to ameliorate one or more of the symptoms of the disease.

65. The method of claim 61, wherein the disease is selected from the group consisting of hypertension, cardiovascular disease, asthma, pulmonary hypertension, inflammatory diseases, ophthalmologic disease, menstrual disorders, obstetric conditions, wounds, gastroenteric disease, renal failure, immunosuppressant-mediated renal vasoconstriction, erythropoietinmediated vasoconstriction endotoxin shock, anaphylactic shock and hemorrhagic shock.

66. The method of claim 61, wherein the disease is selected from the group consisting of hypertension, cardiovascular disease, pulmonary hypertension, erythropoietin-mediated vasoconstriction endotoxin shock, anaphylactic shock and hemorrhagic shock.

67. The method of claim 61, wherein the disease is selected from the group consisting of asthma and inflammatory diseases.

68. A method for inhibiting the binding of an endothelin peptide to endothelin$_A$ (ET$_A$) or endothelin$_B$ (ET$_B$) receptors, comprising contacting the receptors an endothelin peptide and with one or more compounds of claim 1 or salts of the compounds of claim 1, wherein:

the contacting is effected prior to, simultaneously with or subsequent to contacting the receptors with the endothelin peptide.

69. A method for inhibiting the binding of an endothelin peptide to endothelin$_A$ (ET$_A$) or endothelin$_B$ (ET$_B$) receptors, comprising contacting the receptors an endothelin peptide and with one or more compounds of claim 3 or salts of the compounds of claim 3, wherein:

the contacting is effected prior to, simultaneously with or subsequent to contacting the receptors with the endothelin peptide.

70. A method for altering endothelin receptor-mediated activity, comprising contacting endothelin receptors with one or more compounds of claim 1 or salts of the compounds of claim 1.

71. A method for altering endothelin receptor-mediated activity, comprising contacting endothelin receptors with one or more compounds of claim 3 or salts of the compounds of claim 3.

72. A pharmaceutical composition formulated for single dosage administration, comprising an effective amount of one or more compounds of claim 1 or pharmaceutically acceptable salts of the compounds of claim 1, wherein the amount is effective for ameliorating the symptoms of an endothelin-mediated disease.

73. A pharmaceutical composition formulated for single dosage administration, comprising an effective amount of one or more compounds of claim 3 or pharmaceutically acceptable salts of the compounds of claim 3, wherein the amount is effective for ameliorating the symptoms of an endothelin-mediated disease.

74. An article of manufacture, comprising packaging material and a compound of claim 1 or pharmaceutically acceptable salt of a compound of claim 1 contained within the packaging material, wherein the compound or salt therof is effective for antagonizing the effects of endothelin, ameliorating the symptoms of an endothelin-mediated disorder, or inhibiting the binding of an endothelin peptide to an ET receptor with an $IC_{50}$ of less than about 10 µM; and the packaging material includes a label that indicates that the compound or salt thereof is used for antagonizing the effects of endothelin, inhibiting the binding of endothelin to an endothelin receptor or treating an endothelin-mediated disorder.

75. An article of manufacture, comprising packaging material and a compound of claim 3 or pharmaceutically acceptable salt of a compound of claim 3 contained within the packaging material, wherein the compound or salt therof is effective for antagonizing the effects of endothelin, ameliorating the symptoms of an endothelin-mediated disorder, or inhibiting the binding of an endothelin peptide to an ET receptor with an $IC_{50}$ of less than about 10 µM; and the packaging material includes a label that indicates that the compound or salt thereof is used for antagonizing the effects of endothelin, inhibiting the binding of endothelin to an endothelin or treating an endothelin-mediated disorder.

76. The sulfonamide of claim 1 that is N-(4-bromo-3-methyl-5-isoxazolyl)-2-[N-(4-ethylphenyl)carboxamide]thiophene-3-sulfonamide.

77. The method of claim 62, wherein the disease is selected from the group consisting of hypertension, cardiovascular disease, asthma, pulmonary hypertension, inflammatory diseases, ophthalmologic disease, menstrual disorders, obstetric conditions, wounds, gastroenteric disease, renal failure, immunosuppressant-mediated renal vasoconstriction, erythropoietin-mediated vasoconstriction endotoxin shock, anaphylactic shock and hemorrhagic shock.

78. The method of claim 62, wherein the disease is selected from the group consisting of hypertension, cardiovascular disease, pulmonary hypertension, erythropoietin-mediated vasoconstriction endotoxin shock, anaphylactic shock and hemorrhagic shock.

79. The method of claim 62, wherein the disease is selected from the group consisting of asthma and inflammatory diseases.

80. The method of claim 63, wherein the disease is selected from the group consisting of hypertension, cardiovascular disease, asthma, pulmonary hypertension, inflammatory diseases, ophthalmologic disease, menstrual disorders, obstetric conditions, wounds, gastroenteric disease, renal failure, immunosuppressant-mediated renal vasoconstriction, erythropoietin-mediated vasoconstriction endotoxin shock, anaphylactic shock and hemorrhagic shock.

81. The method of claim 63, wherein the disease is selected from the group consisting of hypertension, cardiovascular disease, pulmonary hypertension, erythropoietin-mediated vasoconstriction endotoxin shock, anaphylactic shock and hemorrhagic shock.

82. The method of claim 63, wherein the disease is selected from the group consisting of asthma and inflammatory diseases.

83. The method of claim 64, wherein the disease is selected from the group consisting of hypertension, cardiovascular disease, asthma, pulmonary hypertension, inflammatory diseases, ophthalmologic disease, menstrual disorders, obstetric conditions, wounds, gastroenteric disease, renal failure, immunosuppressant-mediated renal vasoconstriction, erythropoietin-mediated vasoconstriction endotoxin shock, anaphylactic shock and hemorrhagic shock.

84. The method of claim 64, wherein the disease is selected from the group consisting of hypertension, cardiovascular disease, pulmonary hypertension, erythropoietin-mediated vasoconstriction endotoxin shock, anaphylactic shock and hemorrhagic shock.

85. The method of claim 64, wherein the disease is selected from the group consisting of asthma and inflammatory diseases.

86. A method for inhibiting the binding of an endothelin peptide to endothelin$_A$ ($ET_A$) or endothelin$_B$ ($ET_B$) receptors, comprising contacting the receptors an endothelin peptide and with one or more compounds of claim 38 or salts of the compounds of claim 37, wherein:

the contacting is effected prior to, simultaneously with or subsequent to contacting the receptors with the endothelin peptide.

87. A method for inhibiting the binding of an endothelin peptide to endothelin$_A$ ($ET_A$) or endothelin$_B$ ($ET_B$) receptors, comprising contacting the receptors an endothelin peptide and with one or more compounds of claim 39 or salts of the compounds of claim 38, wherein:

the contacting is effected prior to, simultaneously with or subsequent to contacting the receptors with the endothelin peptide.

88. A method for altering endothelin receptor-mediated activity, comprising contacting endothelin receptors with one or more compounds of claim 38 or salts of the compounds of claim 37.

89. A method for altering endothelin receptor-mediated activity, comprising contacting endothelin receptors with one or more compounds of claim 39 or salts of the compounds of claim 38.

90. A pharmaceutical composition formulated for single dosage administration, comprising an effective amount of one or more compounds of claim 38 or pharmaceutically acceptable salts of the compounds of claim 37, wherein the amount is effective for ameliorating the symptoms of an endothelinmediated disease.

91. A pharmaceutical composition formulated for single dosage administration, comprising an effective amount of one or more compounds of claim 38 or pharmaceutically acceptable salts of the compounds of claim 38, wherein the amount is effective for ameliorating the symptoms of an endothelinmediated disease.

92. An article of manufacture, comprising packaging material and a compound of claim 37 or pharmaceutically acceptable salt of a compound of claim 37 contained within the packaging material, wherein the compound or salt therof is effective for antagonizing the effects of endothelin, ameliorating the symptoms of an endothelin-mediated disorder, or inhibiting the binding of an endothelin peptide to an ET receptor with an $IC_{50}$ of less than about 10 μM; and the packaging material includes a label that indicates that the compound or salt thereof is used for antagonizing the effects of endothelin, inhibiting the binding of endothelin to an endothelin receptor or treating an endothelin-mediated disorder.

93. An article of manufacture, comprising packaging material and a compound of claim 38 or pharmaceutically acceptable salt of a compound of claim 38 contained within the packaging material, wherein the compound or salt therof is effective for antagonizing the effects of endothelin, ameliorating the symptoms of an endothelin-mediated disorder, or inhibiting the binding of an endothelin peptide to an ET receptor with an $IC_{50}$ of less than about 10 μM; and the packaging material includes a label that indicates that the compound or salt thereof is used for antagonizing the effects of endothelin, inhibiting the binding of endothelin to an endothelin receptor or treating an endothelin-mediated disorder.

* * * * *

UNITED STATES PATENT AND TRADEMARK OFFICE
CERTIFICATE OF CORRECTION

Page 1 of 5

PATENT NO. : 5,591,761
DATED : January 7, 1997
INVENTOR(S) : CHAN, Ming F.; et al.

It is certified that error appears in the above-identified patent and that said Letters Patent is hereby corrected as shown below:

On the title page, item [54] and Column 1, line 1:
IN THE TITLE:
 In the title, "THIOPHENYL-" should read —THIENYL—.
IN THE ABSTRACT:
 at lines 1, "Thiophenyl-" should read —Thienyl—; and
 at line 4, "thiophenyl-" should read —thienyl—.
IN THE SPECIFICATION:
 at column 6, line 35, delete ", and unsustituted or substituted with any of the preceeding groups";
 at column 7, line 50, "in" should read —In—;
 at column 10, line 66, "i" should read —is—;
 at column 10, line 67, "alkynl" should read —alkynyl—;
 at column 11, line 13, "R$^e$" should read —R$^8$—;
 at column 17, line 37, insert —,— between "cycloalkyl" and "cycloalkenyl";
 at column 17, line 37, insert —,— between "cycloalkenyl" and "cycloalkynyl";
 at column 17, line 38, insert —,— between "OH" and "CN";
 at column 18, line 9, insert —,— after "OH";
 at column 20, line 60, "bioastivity" should read —bioactivity—;
 at column 21, line 42, "225291" should read —225:291—;
 at column 26, line 49, column 31, line 50 and column 32, line 43 "was", each occurrence, should read —were—;
 at column 29, line 64, "carbomethoxy" should read —carboxyl—;
 at column 33, line 20, "2-methoxycarbonylthophene" should read —2-methoxycarbonylthiophene—;
 at column 35, line 23, "N.(" should read —N-(—;
 at column 36, line 7, "m.g." should read —mg—;
 at column 36, line 29, "trimethy" should read —trimethyl—;
 at column 36, lines 34, 37 and 58, "was", each occurrence, should read —were—;
 at column 36, line 63, "D." should read —E.—;
 at column 37, lines 59-60, "sulfonarnide" should read —sulfonamide—;
 at column 38, line 54 and at column 39, line 10, "was", each occurrence, should read —were—;
 at column 41, line 22, "t" should read —at—;
 at column 42, lines 7-8, "(Filep et al. (1991). *Biochem. Biophys. Res. Commun.* 177 171-176." should read —Filep et al. ((1991) *Biochem. Biophys. Res. Commun.* 177:171-176).—;
 at column 42, line 31, "tests" should read —test—; and
 at column 42, line 38, "O2" should read —O$_2$—.

UNITED STATES PATENT AND TRADEMARK OFFICE
CERTIFICATE OF CORRECTION

PATENT NO. : 5,591,761
DATED : January 7, 1997
INVENTOR(S) : CHAN, Ming F. et al.

It is certified that error appears in the above-identified patent and that said Letters Patent is hereby corrected as shown below:

Delete claim 36 without prejudice or disclaimer.

Delete claims 8-11, 14, 16, 19, 21, 23, 25, 28, 35, 86, 87, 88, 89 and 90, and replace with the following claims:

8. A sulfonamide of claim 4, wherein $R^1$ is H, lower alkyl, halide or pseudohalide; and $R^2$ is lower alkyl, lower alkenyl, lower alkynyl, lower haloalkyl, halide, pseudohalide or hydrogen.

9. A sulfonamide of claim 5, wherein $R^1$ is H, lower alkyl, halide or pseudohalide; and $R^2$ is lower alkyl, lower alkenyl, lower alkynyl, lower haloalkyl, halide, pseudohalide or hydrogen.

10. A sulfonamide of claim 4 that has formulae (III):

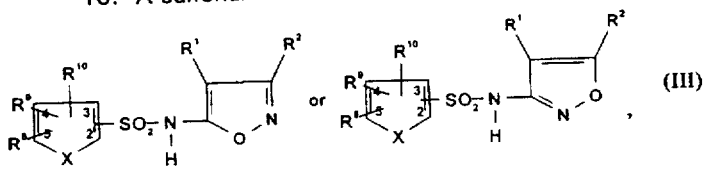

(III)

wherein:

X is O, S, or $NR^{11}$ in which $R^{11}$, which is hydrogen or contains up to about 30 carbon atoms, is selected from the group consisting of hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0-2; and $R^{15}$, which is selected independently from $R^{11}$, is selected from the group consisting of hydrogen, alkyl, alkenyl, alkynyl, aryl, alkylaryl, heterocycle, aralkyl, aralkoxy, cycloalkyl, cycloalkenyl, cycloalkynyl;

and $R^8$, $R^9$ and $R^{10}$ are selected from (i) or (ii):

(i) $R^8$, $R^9$ and $R^{10}$, which each contain hydrogen or up to about 50 carbon atoms, are each independently selected from the group consisting of hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{18}$, $CO_2R^{18}$, SH, $S(O)_nR^{18}$ in which n is 0-2, HNOH, $NR^{18}R^{19}$, $NO_2$, $N_3$, $OR^{18}$, $R^{19}NCOR^{18}$ and $CONR^{19}R^{18}$, in which $R^{19}$ is selected from the group consisting of hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, $C(O)R^{20}$ and $S(O)_nR^{20}$ in which n is 0-2; and $R^{18}$ and $R^{20}$ are each independently selected from the group consisting of hydrogen, alkyl, alkenyl, alkynyl, aryl, alkylaryl, heterocycle, alkoxy, aryloxy, aralkyl, aralkoxy, cycloalkyl, cycloalkenyl or cycloalkynyl; or (ii) any two of $R^8$, $R^9$ and $R^{10}$ form an aromatic or heteroaromatic ring or an alicyclic or heterocyclic ring, which is saturated or unsaturated, containing from about 3 to about 16 members, and the other of $R^8$, $R^9$ and $R^{10}$ is selected as in (i).

UNITED STATES PATENT AND TRADEMARK OFFICE
CERTIFICATE OF CORRECTION

Page 3 of 5

PATENT NO. : 5,591,761

DATED : January 7, 1997

INVENTOR(S) : CHAN, Ming F., et al.

It is certified that error appears in the above-identified patent and that said Letters Patent is hereby corrected as shown below:

11. The sulfonamides of claim 10, in which at least one of $R^8$, $R^9$, and $R^{10}$ is further substituted with one or more substituents selected from Z, which is selected from the group consisting of hydrogen, halide, pseudohalide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0-2, NHOH, $NR^{12}R^{16}$, $NO_2$, $N_3$, $OR^{16}$, $R^{12}NCOR^{16}$ and $CONR^{12}R^{16}$;

$R^{16}$ is selected from the group consisting of hydrogen, alkyl, alkenyl, alkynyl, aryl, alkylaryl, heterocycle, aralkyl, aralkoxy, cycloalkyl, cycloalkenyl and cycloalkynyl;

$R^{12}$ is selected from the group consisting of hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0-2; and $R^{17}$ is selected from the group consisting of hydrogen, alkyl, alkenyl, alkynyl, aryl, alkylaryl, heterocycle, aralkyl, aralkoxy, cycloalkyl, cycloalkenyl or cycloalkynyl.

14. The sulfonamides of claim 10, wherein X is $NR^{11}$.

16. A sulfonamide of claim 11, wherein at least two of $R^8$, $R^9$ and $R^{10}$ are hydrogen, halogen or lower alkyl, and the other is selected from the group consisting of hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{18}$, $CO_2R^{18}$, SH, $S(O)_nR^{18}$ in which n is 0-2, HNOH, $NR^{18}R^{19}$, $NO_2$, $N_3$, $OR^{18}$, $R^{19}NCOR^{18}$ and $CONR^{19}R^{18}$.

19. A sulfonamide of claim 18, wherein at least two of $R^8$, $R^9$ and $R^{10}$ are hydrogen, halogen or lower alkyl, and the other is $C(O)R^{18}$, $CO_2R^{18}$, $NR^{18}R^{19}$, $R^{19}NCOR^{18}$ or $CONR^{19}R^{18}$.

21. A sulfonamide of claim 12, wherein at least two of $R^8$, $R^9$ and $R^{10}$ are hydrogen, halogen or lower alkyl, and the other is selected from the group consisting of hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{18}$, $CO_2R^{18}$, SH, $S(O)_nR^{18}$ in which n is 0-2, HNOH, $NR^{18}R^{19}$, $NO_2$, $N_3$, $OR^{18}$, $R^{19}NCOR^{18}$ and $CONR^{19}R^{18}$.

23. A sulfonamide of claim 22, wherein at least two of $R^8$, $R^9$ and $R^{10}$ are hydrogen, halogen or lower alkyl, and the other is selected from the group consisting of $C(O)R^{18}$, $CO_2R^{18}$, $NR^{18}R^{19}$, $R^{19}NCOR^{18}$ and $CONR^{19}R^{18}$.

25. A sulfonamide of claim 15, wherein at least two of $R^8$, $R^9$ and $R^{10}$ are hydrogen, halogen or lower alkyl, and the other is selected from the group consisting of hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{18}$, $CO_2R^{18}$, SH, $S(O)_nR^{18}$ in which n is 0-2, HNOH, $NR^{18}R^{19}$, $NO_2$, $N_3$, $OR^{18}$, $R^{19}NCOR^{18}$ and $CONR^{19}R^{18}$.

28. A sulfonamide of claim 27, wherein at least two of $R^8$, $R^9$ and $R^{10}$ are hydrogen, halogen or lower alkyl, and the other is selected from the group consisting of $C(O)R^{18}$, $CO_2R^{18}$, $NR^{18}R^{19}$, $R^{19}NCOR^{18}$ and $CONR^{19}R^{18}$.

UNITED STATES PATENT AND TRADEMARK OFFICE
CERTIFICATE OF CORRECTION

Page 4 of 5

PATENT NO. : 5,591,761
DATED : January 7, 1997
INVENTOR(S) : CHAN, Ming F., et al.

It is certified that error appears in the above-identified patent and that said Letters Patent is hereby corrected as shown below:

35. A sulfonamide of claim 8 that has formulae (III):

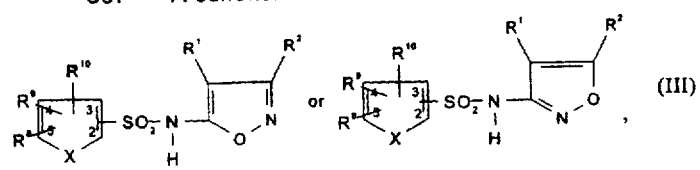

wherein:
X is S; and $R^8$, $R^9$ and $R^{10}$ are selected from (i) or (ii):

(i) $R^8$, $R^9$ and $R^{10}$, which each contain hydrogen or up to about 50 carbon atoms, are each independently selected from the group consisting of hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{18}$, $CO_2R^{18}$, SH, $S(O)_nR^{18}$ in which n is 0-2, HNOH, $NR^{18}R^{19}$, $NO_2$, $N_3$, $OR^{18}$, $R^{19}NCOR^{18}$ and $CONR^{19}R^{18}$, in which $R^{19}$ is selected from the group consisting of hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, $C(O)R^{20}$ and $S(O)_nR^{20}$ in which n is 0-2; and $R^{18}$ and $R^{20}$ are each independently selected from the group consisting of hydrogen, alkyl, alkenyl, alkynyl, aryl, alkylaryl, heterocycle, alkoxy, aryloxy, aralkyl, aralkoxy, cycloalkyl, cycloalkenyl or cycloalkynyl; or (ii) any two of $R^8$, $R^9$ and $R^{10}$ form an aromatic or heteroaromatic ring or an alicyclic or heterocyclic ring, which is saturated or unsaturated, containing from about 3 to about 16 members, and the other of $R^8$, $R^9$ and $R^{10}$ is selected as in (i).

86. A method for inhibiting the binding of an endothelin peptide to endothelin$_A$ ($ET_A$) or endothelin$_B$ ($ET_B$) receptors, comprising contacting the receptors an endothelin peptide and with one or more compounds of claim 37 or salts of the compounds of claim 37, wherein:
the contacting is effected prior to, simultaneously with or subsequent to contacting the receptors with the endothelin peptide.

87. A method for inhibiting the binding of an endothelin peptide to endothelin$_A$ ($ET_A$) or endothelin$_B$ ($ET_B$) receptors, comprising contacting the receptors an endothelin peptide and with one or more compounds of claim 38 or salts of the compounds of claim 38, wherein:
the contacting is effected prior to, simultaneously with or subsequent to contacting the receptors with the endothelin peptide.

88. A method for altering endothelin receptor-mediated activity, comprising contacting endothelin receptors with one or more compounds of claim 37 or salts of the compounds of claim 37.

UNITED STATES PATENT AND TRADEMARK OFFICE
CERTIFICATE OF CORRECTION

PATENT NO. : 5,591,761
DATED : January 7, 1997
INVENTOR(S) : CHAN, Ming F. et al.

It is certified that error appears in the above-identified patent and that said Letters Patent is hereby corrected as shown below:

89. A method for altering endothelin receptor-mediated activity, comprising contacting endothelin receptors with one or more compounds of claim 38 or salts of the compounds of claim 38.

90. A pharmaceutical composition formulated for single dosage administration, comprising an effective amount of one or more compounds of claim 37 or pharmaceutically acceptable salts of the compounds of claim 37, wherein the amount is effective for ameliorating the symptoms of an endothelin-mediated disease.

Signed and Sealed this

Twenty-seventh Day of January, 1998

Attest:

BRUCE LEHMAN

Attesting Officer

Commissioner of Patents and Trademarks